United States Patent
LaVon et al.

[11] Patent Number: 5,938,648
[45] Date of Patent: Aug. 17, 1999

[54] ABSORBENT ARTICLES EXHIBITING IMPROVED INTERNAL ENVIRONMENTAL CONDITIONS

[75] Inventors: Gary Dean LaVon, Middletown, Ohio; Hyun Sung Lim, Chesterfield, Va.; J. Michael McKenna, Hockessin, Del.; George Joseph Ostapchenko, Wilmington, Del.; Shailaja R. Vaidya, Hockessin, Del.; Theodora Beck; John Joseph Curro, both of Cincinnati, Ohio

[73] Assignee: The Procter & Gamble Co., Cincinnati, Ohio

[21] Appl. No.: 08/984,463

[22] Filed: Dec. 3, 1997

[51] Int. Cl.⁶ .................................................... A61F 13/15
[52] U.S. Cl. .................. 604/358; 604/385.1; 604/378; 604/367; 604/370
[58] Field of Search ................................. 604/383, 378, 604/389, 390, 364, 367; 156/290, 167; 428/198, 355

[56] References Cited

U.S. PATENT DOCUMENTS

| H1750 | 9/1998 | Dobrin | 604/383 |
|---|---|---|---|
| 2,075,189 | 3/1937 | Galligan et al. | 154/33 |
| 3,025,199 | 3/1962 | Harwood | 154/46 |
| 3,651,014 | 3/1972 | Witsiepe | 260/75 |
| 3,763,109 | 10/1973 | Witsiepe | 260/75 |
| 3,766,146 | 10/1973 | Witsiepe | 260/75 |

(List continued on next page.)

FOREIGN PATENT DOCUMENTS

| 673646 | 1/1996 | Australia | B32B 27/08 |
|---|---|---|---|
| 0 560 630 | 9/1993 | European Pat. Off. | B32B 27/34 |
| 0 688 826 | 12/1995 | European Pat. Off. | C08L 77/12 |
| 39 02 019 | 9/1990 | Germany | C08L 75/04 |
| 8-041316 | 2/1996 | Japan | C08L 75/04 |
| 8-084749 | 4/1996 | Japan | A61F 13/54 |

(List continued on next page.)

OTHER PUBLICATIONS

U.S. application No. 08/359,986, McCormack et al., filed Dec. 20, 1994.

Thomas R. Ryle, Extrusion Coating and Lamination of Nonwovens, *Principles of Nonwovens,* TS1828.P66, 717–727, 1992.

*Primary Examiner*—Robert A. Clarke
*Assistant Examiner*—Miley Craig Peppers, III
*Attorney, Agent, or Firm*—William Scott Andes

[57] ABSTRACT

The present invention relates to absorbent articles such as diapers, adult incontinence garments, and feminine hygiene products. The present invention further relates to such absorbent articles having outer coverings designed to provide breathability and promote more healthy internal environmental conditions for the wearer. More specifically, the present invention provides an absorbent article comprising (a) a topsheet; (b) a backsheet; and (c) an absorbent core located between the topsheet and the backsheet; wherein the backsheet comprises a non-porous, substantially fluid impermeable, moisture vapor permeable composite sheet material. Preferably, the composite sheet material is oriented such that the film layer of the composite sheet material faces toward said absorbent core. Where the film layer of the composite sheet comprises a substantially hydrophilic elastomer film layer, the substantially hydrophilic elastomer film is preferably located in contact with the fibrous substrate. Where the film layer of the composite sheet comprises a multiple layer film with a substantially hydrophilic elastomer film layer and a substantially hydrophobic elastomer film, the substantially hydrophilic elastomer film is preferably located between the substantially hydrophobic elastomer film and the fibrous substrate. In another embodiment, the film layer may further comprise a third film layer comprising a substantially hydrophobic elastomer film located between the substantially hydrophilic elastomer film and the fibrous substrate. The absorbent article may comprise a disposable diaper.

22 Claims, 9 Drawing Sheets

U.S. PATENT DOCUMENTS

| | | | |
|---|---|---|---|
| 3,848,594 | 11/1974 | Buell | 128/284 |
| 3,860,003 | 1/1975 | Buell | 128/287 |
| 3,904,706 | 9/1975 | Hoeschele | 260/858 |
| 3,911,173 | 10/1975 | Sprauge, Jr. | 427/207 |
| 3,914,488 | 10/1975 | Gorrafa | 428/397 |
| 3,929,135 | 12/1975 | Thompson | 128/287 |
| 3,968,183 | 7/1976 | Hayashi et al. | 260/860 |
| 4,107,364 | 8/1978 | Sisson | 428/196 |
| 4,209,563 | 6/1980 | Sisson | 428/288 |
| 4,324,246 | 4/1982 | Mullane et al. | 128/287 |
| 4,342,314 | 8/1982 | Radel et al. | 128/287 |
| 4,368,295 | 1/1983 | Newton et al. | 525/166 |
| 4,381,781 | 5/1983 | Sciaraffa et al. | 604/372 |
| 4,463,045 | 7/1984 | Ahr et al. | 428/131 |
| 4,493,870 | 1/1985 | Vrouenraets et al. | 428/245 |
| 4,515,595 | 5/1985 | Kievit et al. | 604/385 A |
| 4,573,986 | 3/1986 | Minetola et al. | 604/366 |
| 4,578,072 | 3/1986 | Lancaster | 604/385 |
| 4,578,429 | 3/1986 | Gergen et al. | 525/291 |
| 4,610,678 | 9/1986 | Weisman et al. | 604/368 |
| 4,634,625 | 1/1987 | Franklin | 428/258 |
| 4,662,875 | 5/1987 | Hirotsu et al. | 604/389 |
| 4,663,220 | 5/1987 | Wisneski et al. | 428/221 |
| 4,673,402 | 6/1987 | Weisman et al. | 604/368 |
| 4,695,278 | 9/1987 | Lawson | 604/385 A |
| 4,704,115 | 11/1987 | Buell | 604/385 A |
| 4,707,407 | 11/1987 | Clark et al. | 428/361 |
| 4,710,190 | 12/1987 | Wood et al. | 604/389 |
| 4,725,481 | 2/1988 | Ostapchenko | 428/213 |
| 4,739,012 | 4/1988 | Hagman | 525/92 |
| 4,769,273 | 9/1988 | Hoeschele et al. | 428/215 |
| 4,785,996 | 11/1988 | Ziecker et al. | 239/298 |
| 4,789,699 | 12/1988 | Kieffer et al. | 524/271 |
| 4,795,454 | 1/1989 | Dragoo | 604/385.2 |
| 4,834,735 | 5/1989 | Alemany et al. | 604/368 |
| 4,834,741 | 5/1989 | Sabee | 604/385.2 |
| 4,842,666 | 6/1989 | Werenicz | 156/161 |
| 4,846,815 | 7/1989 | Scripps | 604/391 |
| 4,857,067 | 8/1989 | Wood et al. | 604/389 |
| 4,868,062 | 9/1989 | Hoeschele et al. | 428/423.1 |
| 4,869,724 | 9/1989 | Scripps | 604/389 |
| 4,888,231 | 12/1989 | Angstadt | 428/213 |
| 4,894,060 | 1/1990 | Nestegard | 604/391 |
| 4,908,260 | 3/1990 | Dodia et al. | 428/215 |
| 4,909,803 | 3/1990 | Aziz et al. | 604/385.2 |
| 4,938,752 | 7/1990 | Vrouenraets et al. | 604/370 |
| 4,938,753 | 7/1990 | Van Gompel et al. | 604/385.2 |
| 4,946,527 | 8/1990 | Battrell | 156/60 |
| 4,988,344 | 1/1991 | Reising et al. | 604/368 |
| 4,988,345 | 1/1991 | Reising | 604/368 |
| 5,006,394 | 4/1991 | Baird | 428/138 |
| 5,064,703 | 11/1991 | Frankosky et al. | 428/95 |
| 5,137,537 | 8/1992 | Herron et al. | 8/120 |
| 5,147,345 | 9/1992 | Young et al. | 604/378 |
| 5,151,092 | 9/1992 | Buell et al. | 604/385.2 |
| 5,234,423 | 8/1993 | Alemany et al. | 604/385.2 |
| 5,326,612 | 7/1994 | Goulait | 428/100 |
| 5,330,458 | 7/1994 | Buell et al. | 604/385.1 |
| 5,358,500 | 10/1994 | Lavon et al. | 604/385.2 |
| 5,422,172 | 6/1995 | Wu | 428/230 |
| 5,445,862 | 8/1995 | Kaneko et al. | 428/148 |
| 5,445,874 | 8/1995 | Shehata | 428/252 |
| 5,447,783 | 9/1995 | Horn | 428/216 |
| 5,514,470 | 5/1996 | Haffner et al. | 428/246 |
| 5,518,801 | 5/1996 | Chappell et al. | 428/152 |
| 5,520,980 | 5/1996 | Morgan et al. | 428/246 |
| 5,523,146 | 6/1996 | Bodford et al. | 428/198 |
| 5,532,053 | 7/1996 | Mueller | 428/287 |
| 5,532,054 | 7/1996 | Koba et al. | 428/294 |
| 5,562,983 | 10/1996 | Kono et al. | 428/355 |
| 5,599,420 | 2/1997 | Yeo e tal. | 156/290 |
| 5,599,610 | 2/1997 | Levy | 442/261 |
| 5,865,823 | 2/1999 | Curro | 604/367 |
| B1 3,860,003 | 4/1989 | Buell | 604/385.2 |
| B1 4,662,875 | 4/1989 | Hirotsu et al. | 604/389 |
| B2 3,860,003 | 6/1990 | Buell | 604/385.2 |

FOREIGN PATENT DOCUMENTS

| | | | |
|---|---|---|---|
| 8-108504 | 4/1996 | Japan | A61F 13/15 |
| 8-117270 | 5/1996 | Japan | A61F 13/15 |
| 8-117271 | 5/1996 | Japan | A61F 13/15 |
| 8-117280 | 5/1996 | Japan | A61F 13/15 |
| 8-117281 | 5/1996 | Japan | A61F 13/15 |
| 8-120097 | 5/1996 | Japan | A61F 5/44 |
| 8-126663 | 5/1996 | Japan | A41B 13/04 |
| 2 024 100 | 1/1980 | United Kingdom | 5/2 |
| WO 90/10424 | 9/1990 | WIPO | A61F 13/00 |
| WO 95/16562 | 6/1995 | WIPO | B32B 5/24 |
| WO 95/16746 | 6/1995 | WIPO | C08L 67/02 |
| WO 96/36248 | 2/1996 | WIPO | A41B 9/00 |
| WO 96/39031 | 12/1996 | WIPO | A01N 25/34 |
| WO 96/39032 | 12/1996 | WIPO | A01N 25/34 |
| WO 97/04955 | 2/1997 | WIPO | B32B 3/26 |

ABSORBENT ARTICLES EXHIBITING IMPROVED INTERNAL ENVIRONMENTAL CONDITIONS

FIELD OF THE INVENTION

The present invention relates to absorbent articles such as diapers, adult incontinence garments, and feminine hygiene products. The present invention further relates to such absorbent articles having outer coverings designed to provide breathability and promote more healthy internal environmental conditions for the wearer.

BACKGROUND OF THE INVENTION

Absorbent articles for the management and containment of body exudates have been widely accepted for use by the general public. However, due to the fact that such articles are designed to absorb and contain body exudates, particularly bodily fluids, such articles are often constructed with an outer covering which are substantially fluid and vapor impermeable. While such materials are effective in preventing leakage of bodily fluids onto outer clothing and surrounding surfaces, rapped fluids tend to create a humid environment within the absorbent article. Prolonged exposure to humid environmental conditions, such as those inside such an absorbent article which has been subjected to bodily fluids, have demonstrated a tendency to increase the skin hydration of the wearer thereby increasing the skin sensitivity and possible skin irritation among certain individuals.

To address such concerns, materials have been developed which provide or promote breathability (i.e., exchange of air and/or moisture vapor) through the outer covering to improve the quality of the internal environment. While such materials have shown some promise as a positive step in improving the environmental conditions within absorbent articles, in many instances the property of increased breathability or vapor transmission comes at the expense of increased likelihood of fluid leakage under normal in-use conditions.

Certain polymeric films have been made more acceptable for apparel and personal care applications by creating micropores in the films to make breathable (i.e., moisture vapor permeable) microporous films. In microporous films, moisture is transported through the films by way of small gaps or holes in the film. One notable microporous film composite is made from polytetrafluoroethylene that is adhered to a textile material with an adhesive, as disclosed in British Patent Application No. 2,024,100. Microporous films adhesively bonded to textile substrates have been used in a variety of apparel products, including absorbent articles, as disclosed in PCT Patent Publication Nos. WO 95/16562 and WO 96/39031.

Laminates of a microporous film and a fibrous textile substrate have a number of disadvantages, including that such laminates permit some seepage of fluids when used as the backsheet in an absorbent article. For example, when microporous film laminates are used as the backsheet of a disposable diaper, the backsheet may permit the transmission of some urine through the pores in the backsheet when an infant wearing the diaper sits down. Liquid seepage through microporous film laminates is especially likely to occur when the microporous laminate is exposed to a fluid with a low surface tension, as for example when urine in a diaper is exposed to surfactants within the diaper itself. In addition, the liquid seepage issue worsens as moisture vapor transmission increases. This is a result of an increase in pore size or number of pores.

When fluids seep through the pores of a microporous film, bacteria, viruses, and other microbes can pass through the film along with the fluids. Likewise, the passage of fluids through laminates made with microporous films, whether the fluids are liquid or gaseous, also increases the odors that emanate from such laminates. Microbial adsorbents have been added to some microporous films in an attempt to capture microbes passing through such films, as disclosed in PCT Patent Publication No. WO 96/39031. However, it is difficult to distribute microbial adsorbents throughout a microporous film in a manner that will adsorb all microbes seeping through the holes in the film. Likewise, microbial adsorbents are unlikely to prevent the passage of odors through the pores in a microporous film.

Moisture vapor permeable films comprised of polyether block copolymers, like the film disclosed in U.S. Pat. No. 4,493,870, have an advantage in apparel and personal care applications because such films are non-porous and therefore substantially impermeable to fluids, but they permit the passage of moisture vapor. U.S. Pat. Nos. 4,725,481; 5,422,172; and 5,445,874 disclose that moisture vapor permeable polyether block copolymer films can be attached to a variety of fibrous substrates including polyester, polypropylene and nylon. Bonding methods used to join the polyether block copolymer films to the fibrous substrates include adhesive lamination, thermal lamination and extrusion coating. Adhesive lamination and thermal lamination are generally carried out in a two step process whereby the film is first formed and is subsequently laminated to the fibrous substrate. With extrusion coating, a melted film is extruded directly onto a fibrous substrate and then passed through a nip while the film is still hot in order to press the film into engagement with the fiber network of the fibrous sheet.

Adhesive lamination, thermal lamination and extrusion coating methods have all been used to produce composite sheets of a fibrous nonwoven substrate and a moisture vapor permeable, substantially liquid impermeable film. It has been possible to make such composite sheets with good barrier properties so long as the moisture vapor permeable film is relatively thick (i.e., >25 microns). However, it has not been possible to make such composite sheets with thinner films without sacrificing important barrier properties. Very thin moisture vapor permeable films are desirable in a composite sheet because thinner films facilitate significantly greater flux of moisture vapor through the composite sheet and because thinner films use less of the film material and are accordingly less expensive to produce.

Adhesive lamination is carried out in a post film formation step. For adhesive lamination to be feasible, the moisture vapor permeable film must have enough structure, tensile strength and tear strength such that the film can be formed, wound onto a roll, and later unwound and handled during the adhesive lamination process. It is extremely difficult to handle moisture vapor permeable films less than 25 microns (1 mil) in thickness during the adhesive lamination process without introducing holes into the film. Thus, when adhesive lamination has been used to attempt to make composite sheets with thinner films, the composite sheets have not exhibited the fluid barrier properties (e.g., hydrostatic head, dynamic fluid transmission) desirable for a composite sheet designed for use in absorbent articles or medical apparel.

Thermal lamination of moisture vapor permeable films less than 25 microns thick has similarly resulted in composite sheet materials with inadequate barrier properties. When composite sheets are made by thermally laminating a thin film to a fibrous substrate, the thin film handling problems associated with adhesive lamination described above are encountered. In addition, to carry out a thermal lamination, the film must be subjected to elevated temperatures and pressures so as to soften the film and force it into mechanical engagement with the fibrous substrate. Generally, the peel strength between the film and the fibrous substrate increases with increasing extrusion melt temperatures and increasing nip pressures. Unfortunately, when moisture vapor permeable films with a thickness of less than 25 microns are subjected to the elevated temperatures and pressures needed to obtain adequate peel strength in the composite sheet, small holes develop in the film such that the composite sheet does not exhibit the fluid barrier properties desired in a composite sheet for use in absorbent articles or medical apparel. These small holes can result from non-uniform temperatures throughout the web combined with the high bonding pressures disclosed in the prior art.

Extrusion coating processes disclosed in the prior art are similarly unable to generate a composite sheet with a thin moisture vapor permeable film of less than 25 microns that also has the barrier properties and moisture vapor transmission properties desirable for use in medical apparel and absorbent article applications. In an extrusion coating process, the polymer that forms the film is melted at an elevated temperature to reduce its viscosity such that when the polymer melt is coated onto the fibrous substrate and passed through a nip, the melt is pressed into engagement with the fibrous network of the substrate. Unfortunately, the low viscosity of the melted polymer, the pressure of the nip, and a thinness of the film each contribute to the generation of small holes in the film. In addition, thinner films are more susceptible to fiber protrusion through the film which also contributes to small holes.

Accordingly, there is a need for a composite sheet material that acts as a barrier to fluids, yet is also highly permeable to moisture vapor. There is also a need for a sheet material that readily transmits moisture vapor, but significantly deters the passage of bacteria, viruses and odors associated with such fluids. There is a further need for such a moisture vapor permeable, fluid impermeable composite sheet material that is also durable, strong, and flexible enough to be used in apparel and absorbent articles, and can be produced in an economical fashion, i.e., film extrusion and lamination in one process. Specifically, there is a need for a composite sheet material with a moisture vapor permeable film that is less than 25 microns thick, exhibits excellent moisture vapor transmission, high peel strength, and barrier properties sufficient to prevent passage of liquids under static and dynamic loading conditions. Finally, there is a need for a process for producing such a composite sheet material.

Accordingly, it would be desirable to provide an absorbent article which provides a drier, less humid internal environment for a wearer via the utilization of an outer covering comprising a moisture vapor permeable material.

It would also be desirable to provide such an absorbent article which also exhibits fluid-impervious barrier properties under normal in-use conditions.

It would further be desirable to provide such an absorbent article which exhibits desirable visual and tactile properties.

SUMMARY OF THE INVENTION

The present invention provides an absorbent article comprising (a) a topsheet; (b) a backsheet; and (c) an absorbent core located between the topsheet and the backsheet; wherein the backsheet comprises a non-porous, substantially fluid impermeable, moisture vapor permeable composite sheet material. Preferably, the composite sheet material is oriented such that the film layer of the composite sheet material faces toward said absorbent core. Where the film layer of the composite sheet comprises a substantially hydrophilic elastomer film layer, the substantially hydrophilic elastomer film is preferably located in contact with the fibrous substrate. Where the film layer of the composite sheet comprises a multiple layer film with a substantially hydrophilic elastomer film layer and a substantially hydrophobic elastomer film, the substantially hydrophilic elastomer film is preferably located between the substantially hydrophobic elastomer film and the fibrous substrate. In another embodiment, the film layer may further comprise a third film layer comprising a substantially hydrophobic elastomer film located between the substantially hydrophilic elastomer film and the fibrous substrate. The absorbent article may comprise a disposable diaper.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

Reference will now be made in detail to the presently preferred embodiments of the invention, examples of which are illustrated below.

Breathable Composite Sheet Materials

Figure 1:
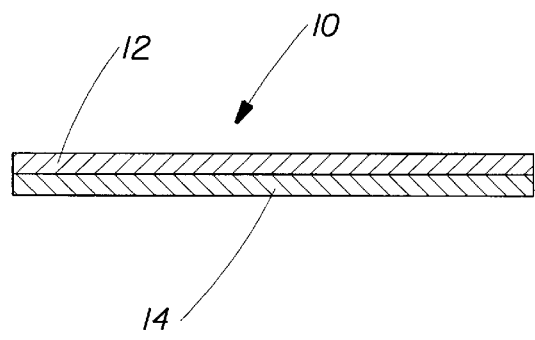
FIG. 1 is a cross-sectional view of the composite sheet structure of the invention.

The liquid impermeable, moisture vapor permeable composite sheet structure of the invention is shown in FIG. 1. The composite sheet 10 is comprised of a fibrous substrate 14 to which a moisture vapor permeable and substantially liquid impermeable film 12 is adhered. Such composite sheets are sometimes referred to as laminate structures. The moisture vapor permeable film is substantially free of pinholes or pores, yet still has a relatively high rate of moisture vapor transmission. As used herein, "pinholes" means small holes inadvertently formed in a film either during manufacture or processing of the film, while "pores" means small holes in a film that are intentionally formed in the film in order to make the film porous to air, moisture vapor or liquids. In an alternative embodiment of the invention shown in FIG. 2, the composite sheet structure may be comprised of a moisture vapor permeable film layer 12 with two fibrous substrates 14 and 16, each comprised of synthetic polymer fibers, adhered on opposite sides of the film layer.

In the preferred embodiment of the invention, the moisture vapor permeable, substantially liquid impermeable film is a polyether block copolymer such as copolymers comprised of block copolyether esters, block copolyether amides, polyurethanes, polyvinyl alcohols, or combinations thereof. The fibrous substrate 14 is preferably comprised of synthetic polymer fibers in a form to which the moisture vapor permeable film can be adhered. The substrate 14 may be a woven or nonwoven structure, but for cost reasons, nonwoven textile structures are preferred for most applications.

The fibrous substrates 14 and 16 should exhibit strength, permeability, and softness properties that are desired for the end use for which the composite sheet is to be applied. For example, where the composite sheet 10 is to be used in an absorbent article, the substrates 14 and/or 16 should preferably have a tensile strength of at least 1 N/cm and an elongation of at least 30% in both the machine and cross directions. The machine direction is the long direction within the plane of the sheet, i.e., the direction in which the sheet is produced. The cross direction is the direction within the plane of the sheet that is perpendicular to the machine direction. More preferably, the fibrous substrates have a tensile strength of at least 1.5 N/cm and an elongation of at least 50% in both the machine and cross directions. Preferably, the fibrous substrate also has a porous structure that enhances both moisture permeability through the composite sheet and physical bonding between the film and substrate layers of the composite sheet.

One preferred nonwoven material for the fibrous substrates 14 and 16 is a fibrous polyolefin nonwoven web. Suitable polyolefin materials include polypropylene and polyethylene spunbonded webs, scrims, woven slit films, carded webs, flashspun webs, and woven or nonwoven sheets comprised of blends of polyolefin fibers or of polyolefin fibers and other fibers. Webs of polyolefin fibers can be made with a variety of desirable properties, including good vapor permeability, flexibility, softness and strength. A polyolefin sheet material that has been advantageously used for the fibrous substrate in the invention is TYPAR® spunbonded polypropylene sheet material. TYPAR® is a registered trademark of DuPont. Another fibrous polyolefin sheet material that has been advantageously used in the composite sheet of the invention is a carded, thermally-bonded polypropylene nonwoven material commercially available from Fiberweb of Simpsonville, S.C., under the trade designation HEC.

Another preferred nonwoven material for the fibrous substrates 14 and 16 is a fibrous nonwoven web comprised of a blend of polyolefin and polyester fibers. Suitable polyolefin fibers include polypropylene and polyethylene staple fibers. Suitable polyester fibers include staple fibers made of polyethylene terepthalate (PET). Webs of polyolefin/polyester fiber blends can be made with a variety of desirable properties, including good vapor permeability, flexibility, softness and strength. One type of polyester fiber that has been blended with polyolefin fibers in the fibrous substrate are shaped polyester fibers with a scalloped-oval cross-section as disclosed in U.S. Pat. No. 3,914,488 to Garrafa (assigned to DuPont), which is hereby incorporated by reference. It is believed that such shaped fibers create channels in the fibrous substrate through which moisture vapor can be more efficiently conveyed through the composite sheet.

Substrates 14 and 16 may alternatively be comprised of webs of other synthetic polymer materials such as polyamides, bicomponent fibers made of a polyolefin and one or more other polymers, or blends of polyolefin fibers and fibers comprised of other synthetic materials or other natural fibers such as cotton or cellulose fibers. The substrates 14 or 16 should have a side on which substantially few fibers extend out from the plane of the fibrous substrate, in other words, a fibrous substrate with a relatively smooth side. This smooth side of the substrate is critical when laminating a very thin film (<25 microns) to the fibrous substrate. If the film is laminated to the surface of a fibrous substrate that is not relatively smooth, fibers that protrude out from the plane of the substrate will likely protrude through the film, which will create pinholes and thereby allow liquid seepage.

Film layer 12 of the composite sheet structure 10 is a moisture vapor permeable and substantially liquid impermeable film. The film layer is preferably extruded and then laminated onto the fibrous substrate 14 in a single process. Film layer 12 comprises a thermoplastic polymer material that can be extruded as a thin, continuous, nonporous, substantially liquid impermeable, moisture vapor permeable film. Layer 12 is preferably comprised primarily of a block polyether copolymer, such as a polyether ester copolymer, a polyether amide copolymer, a polyurethane copolymer, polyvinyl alcohol, or a combination thereof. Preferred copolyether ester block copolymers for film layer 12 are segmented elastomers having soft polyether segments and hard polyester segments, as disclosed in U.S. Pat. No. 4,739,012 (assigned to DuPont). Suitable polyether ester block copolymers are sold by DuPont under the name Hytrel®. Hytrel® is a registered trademark of DuPont. Suitable copolyether amide copolymers for film layer 12 are copolyamides available under the name Pebax® from Atochem Inc. of Glen Rock, N.J., USA. Pebax® is a registered trademark of Elf Atochem, S. A. of Paris, France. Suitable polyurethanes for use in film layer 12 are thermoplastic urethanes available under the name Estane® from The B. F. Goodrich Company of Cleveland, Ohio, USA.

The mixing of the thermoplastic polymer or blends of polymers that comprise the film layer of the sheet structure of the invention can be conducted according to methods and techniques known in the art, e.g., by physical tumble blending followed by extrusion and mixing in a single screw extruder equipped with a mixing head such as those available from Davis-Standard Corp. (Pawcatuck, R.I., USA) or a twin screw compounding extruder such as those available from Warner-Pfliederer (Ramsey, N.J., USA) and Bersdorf Corporation (Charlotte, N.C., USA). Alternatively, loss in weight or volumetric feeders such as those available from K-Tron America (Pitman, N.J., USA) may be used to control the composition being fed to the extruders.

It has now been found that composite sheets with very thin moisture vapor permeable films (less than 25 microns in thickness) can be constructed in a manner such that the thin film is substantially free of pinholes. It has further been found that these moisture vapor permeable films can be attached to the fibrous substrate of the composite sheet in a way that the composite sheet retains a very high rate of moisture vapor transmission. In order to construct a composite sheet of a fibrous substrate and a very thin moisture vapor permeable film, it is necessary that the film extrusion and lamination processes be conducted in a single step so as to make independent handling of the thin film unnecessary. In order to prevent the formation of pinholes during lamination, it has been found that the pressure applied to the film during the lamination process must be kept low in order to prevent the formation of non-uniform thin areas in the film where pinholes are likely to develop, especially due to impact related forces on the film.

Several methods have been found for making a composite sheet material with good peel strength between a thin moisture vapor permeable film and a fibrous substrate without the application of high pressure during the lamination process. According to one preferred process for making the composite sheet, an adhesive is applied to the surface of the fibrous substrate to which the moisture vapor permeable film is to be attached prior to application of the film. The adhesive is preferably applied to the substrate in a dispersed spray pattern at a basis weight of between 3.2 and 38.7 mg/cm$^2$ (0.5 and 6 mg/in$^2$). It is important that the applied adhesive cover less than 75%, and more preferably less than 50%, and most preferably less than 25%, of the surface of the fibrous substrate so that the film layer coated over the adhesive will be discretely bonded to the fibrous substrate and the adhesive will not significantly reduce the moisture vapor transmission rate of the composite sheet. When an adhesive is used to help bond the film layer to the fibrous substrate of the composite sheet, it is preferred that the substrate be made of a material that is not compatible with the polymer of the moisture vapor permeable film. "Compatibility" of thermoplastic materials is an art-recognized term that refers, generally, to the degree to which the thermoplastic materials are miscible and/or interact with each other. Similarly, "incompatible" materials, as used herein, means polymer materials that are substantially immiscible or do not interact with each other. Incompatible materials do not wet each other well, nor do they adhere well to each other, even when heated. For example, when an adhesive is used to attach a copolyether ester elastomer film to a fibrous substrate, the preferred material for the fibrous substrate would be made of an incompatible polymer such as a polyolefin.

Figure 3:
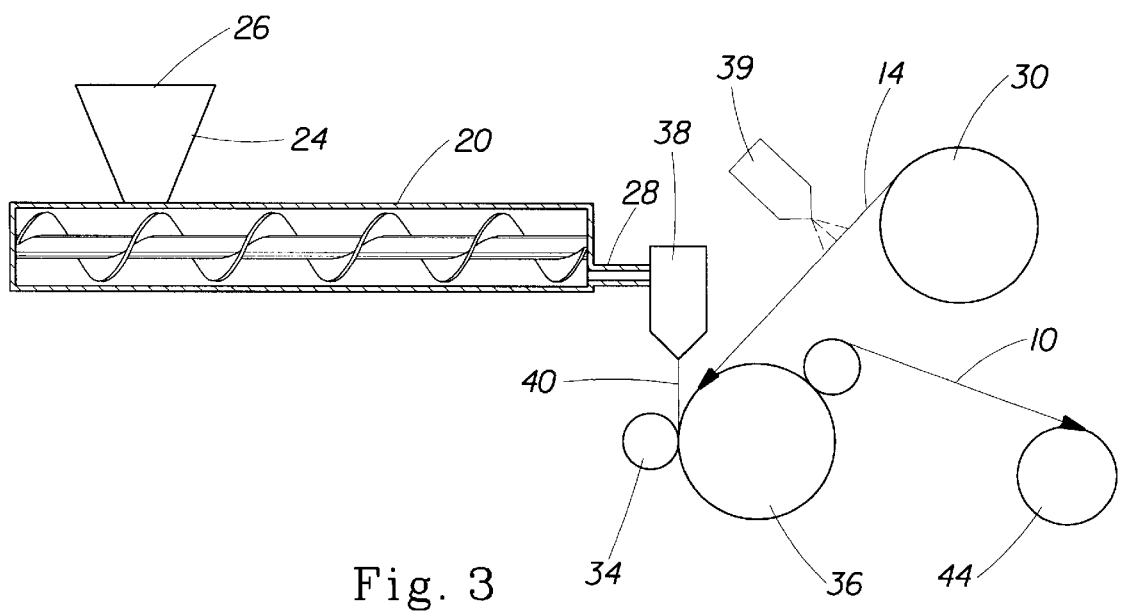
FIG. 3 is a schematic representation of a process by which the composite sheet structure of the invention is made.
Figure 4:
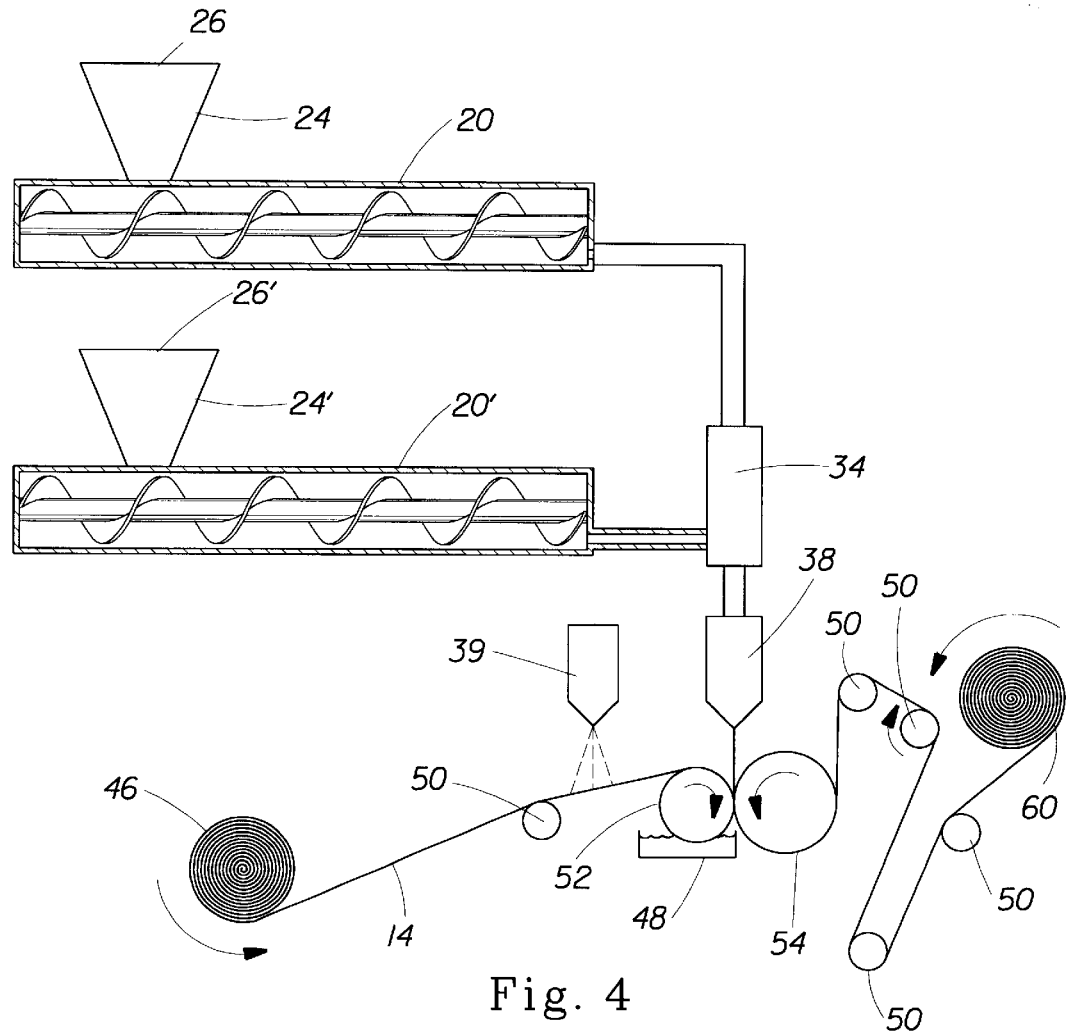
FIG. 4 is a schematic representation of another process by which the composite sheet structure of the invention is made.

A preferred adhesive is a pressure sensitive hot melt adhesive such as a linear styrene isoprene styrene ("SIS") hotmelt adhesive, but it is anticipated that other adhesives, such as polyester of polyamide powdered adhesives, hotmelt adhesives with a compatibilizer such as polyester, polyamide or low residual monomer polyurethanes, other hotmelt adhesives, or other pressure sensitive adhesives could be utilized in making the composite sheet of the invention. Preferably the adhesive is applied to the surface of the fibrous sheet by an optional glue applicator 39, as shown in FIGS. 3 and 4, just before the polymer melt that will form the moisture vapor permeable film layer is extruded onto the substrate. Applicator 39 may comprise a Series 6000 Melter and CF215 Applicator from the Nordson Corporation of Norcross Ga. Alternatively, the adhesive may be applied to the fibrous substrate and then covered with a release paper and rolled up for storage and subsequent film lamination in another step. The moisture vapor permeable film can then be extrusion coated over the adhesive and bonded to the fibrous substrate as described in detail below. With this approach, it is believed that the heat from the film melt is sufficient to soften the adhesive in order to promote bonding.

According to another preferred process for making a composite sheet material with good peel strength between a thin moisture vapor permeable film and a fibrous substrate that does not require the application of high pressure during the lamination process, the film is extrusion coated directly onto the fibrous substrate without the introduction of a separate adhesive between the fibrous substrate and the film. In order to obtain good peel strength in the absence of an adhesive or the application of high pressure, the fibrous substrate is made with a blend of both fibers that are compatible with the polymer of the moisture vapor permeable film and fibers that are incompatible with the film. For example, if the film is a copolyether ester elastomer, the fibrous substrate preferably includes both compatible polyester fibers and incompatible polyolefin fibers. Good bonding can be achieved between a copolyether ester film and the polyester fibers of the fibrous substrate without the application of a high pressure bonding pressure to the film. However, it has been found that if the fibrous substrate includes too high of a percentage of highly compatible fibers, the film bonds to so many of the fibers of the substrate that the transmission of moisture vapor through the composite sheet material is reduced significantly. This reduction in the moisture vapor transmission rate is believed to be related to the film to fiber bond area because the bonded areas will have a significantly reduced moisture vapor transmission rate. Therefore, increasing the film to fiber bond area reduces the moisture vapor transmission rate. As illustrated in Examples 17–21 below, when a copolyether ester elastomer film is extrusion coated on various fibrous substrates, peel strength is improved when the substrate includes polyester fibers. Examples 30–41 illustrate that moisture vapor transmission goes down if the percentage of polyester fibers in the substrate gets too high.

In an extrusion coating process, a uniform molten extrudate is coated on the fibrous substrate. The molten polymer and the substrate are brought into more intimate contact as the molten polymer cools and bonds with the substrate. Such contact and bonding are normally enhanced by passing the layers through a nip formed between two rolls. Alternatively, the molten polymer may be pulled into contact with the fibrous substrate by passing the coated substrate over a suction inlet such that the vacuum pulls the molten polymer into contact with the substrate as the polymer cools and bonds with the substrate. The bonding may be further enhanced by subjecting the surface of the substrate that is to contact the film to surface treatment, such as corona treatment, as is known in the art and described in *Modern Plastics Encyclopedia Handbook*, p. 236 (1994), which is hereby incorporated by reference.

One preferred means for applying the film layer 12 to the substrate 14 is illustrated in FIG. 3. As can be seen in FIG. 3, the thermoplastic polymer is fed in pellet form, along with any additives, into the inlet 26 of the extruder hopper 24. The polymer is melted and mixed in the screw extruder 20 at a screw speed in the range of 10 to 200 rpm, depending on the dimensions of the extruder and the properties of the polymer. The melted mixture is discharged from the extruder under pressure through the heated line 28 to a flat film die 38. The polymer is discharged at a temperature above the melting temperature of the mixture, and preferably at a temperature in the range of 180° to 240° C. The polymer extrusion melt 40 discharging from the flat film die 38 coats the fibrous substrate 14 which is fed from supply roll 30. As discussed above, an adhesive applicator 39 may be used to apply an adhesive to the surface of the fibrous substrate 14 just before the substrate is coated with the extrusion melt 40.

Preferably, the substrate passes under the die at a speed that is coordinated with the speed of the extruder so as to obtain a very thin film thickness of less than 25 microns. The coated substrate enters a nip formed between the rolls 34 and 36, which rolls are maintained at a temperature selected to obtain a composite sheet with a desired peel strength and moisture vapor permeability. The temperature of the rolls 34 and 36 is within the range of 10° to 120° C. Higher roll temperatures have been found to yield a composite sheet with a higher peel strength, while lower roll temperatures have been found to yield composite sheets with a higher moisture vapor permeability. Preferably, roll 34 is a smooth rubber roller with a low-stick surface coating while the roll 36 is a metal roll. A textured embossing roll may be used in place of the metal roll for the roll 36 if a composite sheet with a more textured film layer (and higher surface area) is desired. Passing the coated substrate through the nip formed between cooled rolls 34 and 36 quenches the polymer melt while at the same time compressing the polymer melt 40 into contact with the fibers of the fibrous substrate 14.

The pressure within the nip must be low such that thin spots or pinholes are not formed in the film as the substrate and film pass between the rolls 34 and 36. In the apparatus shown in FIG. 3, pressure cylinders (not shown) are used to apply force to the rolls 34 and 36 which, in turn, generates pressure within the nip. In the apparatus shown in FIG. 3, cylinder pressures of 552 kPa (80 psi) results in the application of a force of 172 N/linear cm along the length of the 20 inch long rolls; cylinder pressures of 414 kPa (60 psi) generate a force of 129 N/linear cm on the rolls; cylinder pressures of 276 kPa (40 psi) generate a force of 86 N/linear cm on the rolls; cylinder pressures of 138 kPa (20 psi) generate a force of 43 N/linear cm on the rolls; and cylinder pressures of 35 kPa (5 psi) generate a force of 11 N/linear cm on the rolls. When thin moisture vapor permeable films are to be bonded on the apparatus shown in FIG. 3, it is preferred that a force of less than 50 N/linear cm be applied to the rolls.

Figure 2:
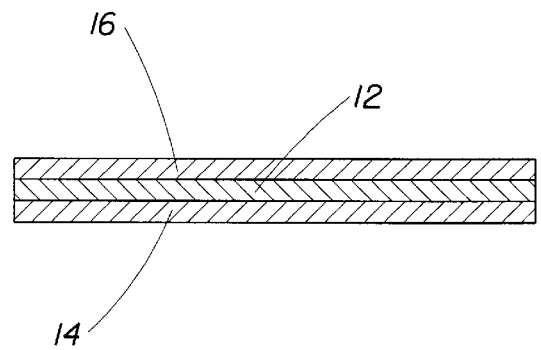
FIG. 2 is a cross-sectional view of a composite sheet structure according to an alternative embodiment of the invention.

When the polymer melt cools, it forms the film layer 12 of composite sheet 10, which composite sheet is collected on a collection roll 44. If a trilaminate product like that shown in FIG. 2 is desired, an additional substrate material 16 may be in the same manner, be laid on the other side of the extruded polymer melt 40 as the polymer passes between rolls 34 and 36.

Alternatively, a vacuum process can be applied in order to lightly contact the polymer melt and the fibrous substrate material. The vacuum process is similar to conventional extrusion coating except that vacuum is used to bond the two substrates instead of nip rolls. The film is sucked onto the fibrous substrate by applying a vacuum force against the underside of the substrate. The vacuum process optimizes adhesion while also producing products with good loft and hand.

According to another embodiment of the invention, the film layer 12 may be a moisture vapor permeable, substantially liquid impermeable multiple layer film structure. Such a film may be coextruded with layers comprised of the one or more of the above described preferred moisture vapor permeable film materials described herein. Such multiple layer moisture permeable films are disclosed in U.S. Pat. No. 4,725,481 (assigned to DuPont), which is hereby incorporated by reference. Multiple layer films are especially useful in the composite sheet of the invention where it is desirable for the film layer 12 to have different properties on its different sides. For example, a composite sheet can be made with a bicomponent film layer 12 having one side made of a moisture vapor permeable polymer material that thermally bonds well to the fibrous substrate 14 and an opposite side comprised of another moisture vapor permeable polymer that bonds well to materials to which the composite sheet is to be applied. It is anticipated that a moisture vapor permeable film of three or more co-extruded layers could be utlilzed, as disclosed in U.S. Pat. No. 5,447,783 to Horn (assigned to DuPont) for the film layer of the composite sheet of the invention in order to obtain an overall desired set of physical and aesthetic properties for the composite sheet.

An alternative apparatus for extrusion coating a multiple layer polymer melt onto a fibrous substrate is schematically illustrated in FIG. 4. As can be seen in FIG. 4, one thermoplastic polymer is fed in pellet form, along with any additives, into the inlet 26 of the extruder hopper 24, while another thermoplastic polymer is fed in pellet form, along with any additives, into the inlet 26' of the extruder hopper 24'. The polymer is melted and mixed in the screw extruders 20 and 20' at screw speeds in the range of 5 to 200 rpm, depending on the dimensions of the extruders and the properties of the polymer. The melted mixture is discharged from the extruder under pressure through heated lines to a melt combining block 34 where a multiple layer melt is formed that is extruded as a multiple layer film through the flat film die 38. The polymer is discharged from the film die 38 at a temperature above the melting temperature of the polymer mixture, and preferably at a temperature in the range of 180° to 240° C. The polymer melt 40 discharging from the flat film die 38 coats the fibrous substrate 14 provided from a supply roll 46. As discussed above, an adhesive applicator 39 may be used to apply an adhesive to the surface of the fibrous substrate 14 that is to be coated with the polymer melt 40.

Preferably, the fibrous substrate 14 in the apparatus and process illustrated in FIG. 4 passes under the die 38 at a speed that is coordinated with the speed of the extruder so as to obtain a very thin film thickness of less than 25 microns. The coated substrate enters a nip formed between the rolls 52 and 54, which rolls are maintained at a temperature selected to obtain a composite sheet with a desired peel strength and moisture vapor permeability. Preferably, roll 52 is a smooth rubber roller with a low-stick surface coating while the roll 54 is a metal roll. Roll 52 may be cooled by a water bath 48. When the polymer melt cools, it forms the film layer 12 of composite sheet 10, which composite sheet is collected on a collection roll 60. Idler rolls 50 maintain tension on the fibrous substrate and the composite sheet throughout the composite sheet formation process.

According to another embodiment of the invention, a thin moisture vapor permeable film could be used in conjunction with a microporous film to form a laminate film structure. Such a structure overcomes a number of the drawbacks associated with microporous films, namely bacteria and liquid seepage and high moisture impact values, without sacrificing the relatively high MVTR values, often >3,000 g/m$^2$/24 hr, obtainable with some microporous films. The moisture vapor permeable films of the composite sheet of the present invention can be made compatible with polyolefin nonwoven materials and can also be made compatible with current microporous film compositions, such as those of polyolefinic composition. The moisture vapor permeable film layer of the composite sheet of the present invention and a microporous film can be joined via adhesive lamination or by direct extrusion coating. The moisture vapor permeable film could be combined with a fibrous substrate in a fashion consistent with the present invention. This fibrous substrate and moisture vapor permeable substantially liquid impermeable film can be joined to a microporous film in a fashion consistent with the present invention, such that the nonwoven fibrous substrate will be bonded to the first side of the moisture vapor permeable, substantially liquid impermeable film layer and the microporous film will be laminated to the opposing side of the film layer.

The composite sheet 10 is especially useful as a component in disposable absorbent articles. As used herein, the term "absorbent article" refers to devices which absorb and contain body exudates, and, more specifically, refers to devices which are placed against or in proximity to the body of the wearer to absorb and contain the various exudates discharged from the body. Absorbent articles include disposable diapers, incontinence briefs, incontinence undergarments, incontinence pads, feminine hygiene garments, training pants, pull-on garments, and the like. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). Composite sheet 10 has physical properties that make the sheet especially useful as the outside "backsheet" of a disposable absorbent article, which properties include the composite sheet material's permeability to moisture vapor, its substantial impermeability to liquids, and its strength and durability. The ability of the composite sheet 10 to readily transmit moisture vapor means that hygiene products incorporating the composite sheet 10 as the product's backsheet material are comfortable to the wearer. The composite sheet's impermeability to fluids allows the sheet to completely contain bodily fluids even when the sheet is subjected to a dynamic impact of the type experienced when a baby or other person wearing a wet absorbent article sits down hard. The strength and durability of the composite sheet 10 permits the sheet to remain intact even after being stretched, rolled and pulled in the process of manufacturing an absorbent article.

It is believed that the moisture vapor transmission rate ("MVTR") of a composite sheet material used as the backsheet of an absorbent article is important in reducing humidity and temperature inside the absorbent article, thereby potentially reducing the incidence of heat rash and other skin problems associated with such environmental conditions. For example, in order to reduce rash inducing humidity and heat buildup within a disposable absorbent article, it has been found that at least a portion of the article's backsheet, and preferably the entire backsheet, should have a moisture vapor transmission rate of at least about 1500 g/m²/24 hr, as measured by the desiccant MVTR measurement method described in the examples below. The composite sheet material of the present invention is capable of delivering an MVTR, as measured by the desiccant method, of at least about 2800 g/m²/24 hr, and composite sheets according to the invention can deliver an MVTR greater than 4000 g/m²/24 hr.

In the composite sheet of the present invention, moisture vapor transmission is enhanced because the moisture vapor permeable film layer 12 is extruded directly onto the nonwoven substrate 14. This direct extrusion improves moisture transmission for a number of reasons. First, direct extrusion makes it possible to make composite sheets with very thin film layers of less than 25 microns in thickness. These thin films are highly permeable to moisture vapor but they are still substantially impermeable to liquids. Second, because the pressure applied against the film layer 12 during the extrusion coating process is very low, the film layer can be made as thin as 7 microns without risk of pinholes. Thus, an extremely thin film can be bonded to the substrate without risking loss of liquid barrier properties. Third, because the film layer is discreetly bonded to the fibrous substrate, whether by adhesive lamination or by thermal lamination using a substrate fiber blend that includes compatible fibers, such that significant portions of the film layer are not bonded to the fibers of the fibrous substrate, moisture vapor transmission can be significantly increased.

The composite sheet of the present invention exhibits the important property that it is substantially impermeable to liquids under conditions that are normally associated with the use of absorbent articles and protective medical apparel. The liquid impermeability of the composite sheet 10 has been characterized according to a number of tests, including a liquid moisture seepage test, a dynamic barrier test, a hydrostatic head test, and a number of microbial barrier tests.

The liquid moisture seepage test visually demonstrates the substantial liquid impermeability of the composite sheet 10. As described in the example below, this test determines whether a solution of food dye, isopropyl alcohol and water passes through a sheet material. As can be seen in Examples 17–20 below, the dye in alcohol solution did not pass through the composite sheet 10 of the present invention. On the other hand, when the same test was conducted on a sheet comprised of a microporous film laminated to a nonwoven substrate, dye solution seepage was apparent (Comparative Example 1).

The dynamic fluid impact test demonstrates the ability of the composite sheet 10 to resist liquid transmission. The dynamic fluid impact test described in the examples below is designed to mimic the energy per unit area that an infant imparts to a diaper backsheet when abruptly going from a standing to a sitting position. Suitable sheet materials for a diaper backsheet should exhibit substantially no dynamic fluid transmission (i.e., less than 1 g/m²) when subjected to an impact energy of about 1000 joules/m², as is the case for the composite sheet 14 of the invention. More preferably, diaper backsheets exhibit substantially no dynamic fluid transmission when subjected to an impact energy of 2400 joules/m² or more. As reported in Examples 1–20 below, the composite sheet of the invention passed less than 0.5 g/m² of water when subjected to an impact energy of about 2400 joules/m².

The ability of the composite sheet 10 to act as a barrier to liquids also prevents the passage of most odors, bacteria, or viruses through the sheet. When a microporous film was tested according to a bacteria flux test used for evaluating porous sterile packaging materials (ASTM F 1608-95) (Comparative Example 1), the material did not pass this test because bacteria was found to pass through the sheet. On the other hand, the composite sheet 10 of the invention, by being impermeable to air during a one hour air porosity test (See Gurley Hill porosity data in Examples 17–25), satisfies the microbial barrier requirement for impermeable sterile packaging materials, as set forth in ISO standard 11607, section 4.2.3.3. As can be seen in Example 17 below, the composite sheet 10 has also been shown to prevent the passage of viruses when tested according to ASTM F1671. ASTM F1671 measures the resistance of materials used in protective clothing to penetration of blood-borne viruses such as the Hepatitis B virus (HBV), the Hepatitis C virus (HCV), and the Human Immunodeficiency Virus (HIV) that causes Acquired Immune Deficiency Syndrom (AIDS). This method measures passage of the surrogate Phi-X174 bacteriophage, which is similar in size to the HCV virus and smaller than the HBV and HIV viruses, through a sheet material.

The strength and durability of composite sheet 10 makes this sheet especially suitable for absorbent article and apparel products. This strength and durability allow the composite sheet 10 to remain intact even after being stretched, rolled, compressed and pulled during the process of manufacturing an absorbent article or apparel product. It is also important that the composite sheet be strong and durable enough to remain intact when stretched, pulled and wetted during wearing of an absorbent article or apparel product made using composite sheet 10 as the sheet material. The strength and durability of composite sheet 10 has been characterized in terms of (1) tensile strength, (2) the degree to which the sheet will stretch before breaking (known as "elongation"), and (3) the amount of force required to peel the moisture vapor permeable film from the fibrous substrate of the composite sheet (known as "peel strength" or "delamination strength").

Tensile strength is determined by measuring the tensile force required to rupture a sample of sheet material. Elongation is a measure of the amount that a sample of sheet material will stretch under tension before the sheet breaks. The elongation is the length just prior to break expressed as a percentage of the original sample length. Preferably, a composite sheet material that is to be used as the backsheet in an absorbent article has a tensile strength of at least 1 N/cm and an elongation of at least 30% in both the machine and cross directions. More preferably, if the composite sheet of the invention is to be used as the backsheet in an absorbent article, it should have a tensile strength of more than 1.5 N/cm and an elongation of at least 50% in both machine and cross directions. In the composite sheet of the present invention, the tensile properties and elongation properties of the composite sheet are largely dependent on the tensile and elongation properties of the fibrous substrate. A sheet material with the preferred tensile strength and elongation remains intact when wrapped around rollers at high speed during manufacture of absorbent articles. The elongation also makes the articles more comfortable to wearers because the articles have some give so as to be more conformable to a wearer's body shape because a sheet material with this elongation generally has some elasticity. As can be seen in Examples 17–20 below, the composite sheet 10 of the invention has a tensile strength of about 6 N/cm in the machine direction and about 1.4 N/cm in the cross direction, and an elongation of about 26% in the machine direction and about 55% in the cross direction. The preferred polyether block copolymer film of the invention provides a degree of elasticity to a composite sheet material that makes the sheet especially useful in an absorbent article.

Peel strength is a measure of the force required to delaminate the moisture permeable film from the fibrous substrate of a composite sheet. When the composite sheet 10 is used as a backsheet in a disposable absorbent article, such as a diaper, it is important that the composite sheet have a peel strength of at least 0.15 N/cm, and more preferably at least 0.20 N/cm, and most preferably at least 0.50 N/cm, so that the sheet will not delaminate during manufacture of the article or during use. Such a peel strength is especially difficult to achieve when low pressure is applied at the nip to bond the film and the fibrous substrate because the composite exhibits reduced mechanical entanglement, and therefore reduced peel strength. Furthermore, adequate peel strength is even more difficult to achieve when the moisture vapor permeable film is chemically incompatible with the fibrous substrate, as is the case when a moisture permeable film comprised solely of a polyether ester block copolymer is coated on a polyolefin-based substrate. "Compatibility" of thermoplastic materials is an art-recognized term that refers, generally, to the degree to which the thermoplastic materials are miscible and/or interact with each other. Similarly, "incompatible" materials, as used herein, means polymer materials that are substantially immiscible or do not interact with each other. Incompatible materials do not wet each other well, nor do they adhere well to each other, even when heated.

The film layer in sheet structures according to the invention may additionally contain conventional additives, such as pigments and fillers (e.g. $TiO_2$, calcium carbonate, silicas, clay, talc) and stabilizers, such as antioxidants and ultraviolet absorbers. These additives are used for a variety of purposes, including reducing the cost of the film layer of the composite sheet structure, and altering the morphology of the film layer of the sheet structure. However, such additives have been found to reduce moisture vapor transmission through the sheet structure. It is important to maintain the amount of additive in the film at a level that does not result in a moisture vapor transmission rate for the sheet that falls outside of the range required for a particular application. The film layer may be comprised of between 0.01% and 30% of additive material, and more preferably between 0.5% and 7% of an inert filler material.

In terms of approaches to bond the composite sheet material to other components of an absorbent article, and more particularly to bond the moisture vapor permeable, liquid impermeable film layer of the composite sheet to other components, it has been observed that only certain methods of bonding will form bonds of sufficient strength to survive forces encountered in normal use, particularly after the film layer has been subjected to fluid contact and has absorbed fluid. Without wishing to be bound by theory, it is presently believed that the moisture vapor permeable film layers of interest in accordance with the present invention provide the desired superior performance properties in terms of moisture vapor transmission due to their comparatively high moisture content under in-use conditions. This comparatively high moisture content, however, is presently believed to have negative implications on the bond strength of the bond between certain conventional hot melt adhesives and the film layer.

One approach which has proven satisfactory is to utilize a polyurethane-based adhesive in accordance with the conventional adhesive application techniques and equipment generally well known in the art, such as described above. Another approach, which is presently preferred, is to utilize the multiple layer, co-extruded film layer described above with reference to the aforementioned and incorporated U.S. Pat. No. 4,725,481 to Ostapchenko, which disclosed a multiple layer film having a hydrophobic layer on the side of the film that was bonded to a nonwoven material and a hydrophilic layer on the opposite side of the film. Applicants have now found it beneficial to utilize a multiple layer moisture vapor permeable film wherein the multiple layer film structure (in a bi-layer execution) is extruded onto a fibrous substrate material with the comparatively more hydrophobic elastomer layer facing outwardly from the substrate and the comparatively more hydrophilic elastomer layer facing toward the substrate. For a given thickness, the hydrophobic elastomer layer typically exhibits a lower MVTR performance than the hydrophilic elastomer layer due to its comparatively lower moisture content under in-use conditions. However, when employed in a comparatively thin layer, the effect of the hydrophobic lower moisture content film layer does not signficantly diminish the MVTR performance of the overall composite sheet.

Due to the comparatively low moisture content of the hydrophobic elastomer layer, conventional hot melt adhesives and bonding techniques may be utilized to successfully form bonds of adequate strength between the composite sheet and other components of the absorbent article even when the film has been wetted. Accordingly, by utilizing a co-extruded, multiple layer, multi-chemistry film layer, a composite sheet can be provided that exhibits both the desired performance properties for the composite sheet of the present invention and can be bonded to other components of absorbent articles via conventional adhesive bonding techniques. (See Examples 17–20 below.)

Quite unexpectedly, additional performance benefits have been discovered through the use of multiple layer films in composite sheets used in constructing absorbent articles. More particularly, the use of a multiple layer film comprising a three-layer structure with a hydrophobic elastomer layer on both facing surfaces surrounding a hydrophilic elastomer layer is believed to deliver improved tactile qualities when extruded onto a fibrous substrate to form a composite sheet. Again without wishing to be bound by theory, it is believed that the comparatively lower moisture content of the hydrophobic film layers results in a drier tactile impression when the fibrous substrate layer is touched or palpated, particularly when the fibrous substrate layer is comparatively thin. Such a multiple layer (tri-layer) embodiment of a composite sheet material would therefore provide both an improved bondability with conventional adhesive techniques and an improved tactile impression from the side of the fibrous substrate layer. Optionally, as discussed above, truly dual-sided configurations could be constructed analogously to FIG. 2 wherein the multiple layer/tri-layer film structure is faced on both sides with a fibrous substrate layer. Optionally, as discussed above, truly dual-sided configurations could be constructed analogously to FIG. 2 wherein the multiple layer/tri-layer film structure is faced on both sides with a fibrous substrate material to provide an enhanced tactile impression from both sides. Such an execution is believed to be particularly desirable for such applications as leg cuffs, waistbands, side panels, and other aspects of absorbent articles such as diapers where a wearer may contact both opposing surfaces of the composite sheet material.

The following non-limiting examples are intended to illustrate the product and process of the invention and not to limit the invention in any manner.

EXAMPLES

In the description above and in the non-limiting examples that follow, the following test methods were employed to determine various reported characteristics and properties. ASTM refers to the American Society for Testing and Materials, TAPPI refers to the Technical Association of Pulp and Paper Industry, and ISO refers to the International Organization for Standardization.

Basis weight was determined by ASTM D-3776, which is hereby incorporated by reference, and is reported in g/m$^2$.

Composite Sheet Thickness was determined by ASTM method D 1777-64, which is hereby incorporated by reference, and is reported in microns.

Film Thickness, is reported in microns, and was determined as follows:

$$\text{Film thickness} = \frac{(\text{composite sheet sample weight}) - (\text{substrate basis weight})(\text{sample area})}{(\text{sample area})(\text{density of film material})}$$

Tensile strength was determined by ASTM D 1682, Section 19, which is hereby incorporated by reference, with the following modifications. In the test a 2.54 cm by 20.32 cm (1 inch by 8 inch) sample was clamped at opposite ends of the sample. The clamps were attached 12.7 cm (5 in) from each other on the sample. The sample was pulled steadily at a speed of 5.08 cm/min (2 in/min) until the sample broke. The force at break was recorded in Newtons/cm as the breaking tensile strength.

Elongation to Break of a sheet is a measure of the amount a sheet stretches prior to failure (breaking)in a strip tensile test. A 1.0 inch (2.54 cm) wide sample is mounted in the clamps—set 5.0 inches (12.7 cm) apart—of a constant rate of extension tensile testing machine such as an Instron table model tester. A continuously increasing load is applied to the sample at a crosshead speed of 2.0 in/min (5.08 cm/min) until failure. The measurement is given in percentage of stretch prior to failure. The test generally follows ASTM D1682-64.

Peel strength is measured according to a test that generally follows the method of ASTM D882-83, which is hereby incorporated by reference. The test was performed used a constant rate of extension tensile testing machine such as an Instron table model tester. A 2.54 cm (1.0 in) by 20.32 cm (8.0 in) sample is delaminated approximately 3.18 cm (1.25 in) by initiating a separation between the fibrous substrate and the moisture vapor permeable film. The separated sample faces are mounted in the clamps of the tester which are set 5.08 cm (2.0 in) apart. The tester is started and run at a cross-head speed of 50.8 cm/min (20.0 in/min). The computer starts picking up readings after the slack is removed, nominally a 5 gram pre-load. The sample is delaminated for about 12.7 cm (5 in) during which sufficient readings are taken to provide a representative average of the data. The peak load and average peel strength is given in N/cm. For samples that are peeled the entire 5 inches the average peel strength is considered to be the peel strength. For samples that do not peel the entire 5 inches due to either full bond conditions or failures in the substrates, the peak load is considered to be the peel strength.

Bond Strength is a measure of the adhesive bond strength between a composite sheet and a 1.2 mil polyethylene film. This is also defined as the strength of the adhesive bond used to construct absorbent articles wherein an adhesive is used to join other materials to the composite structure. Samples were prepared by applying a conventional hotmelt adhesive useful in absorbent article construction to the film side of the composite structure. The adhesive can be any adhesive useful in constructing absorbent articles, one such adhesive useful in article construction is designated as H2031 available from AtoFindley Adhesives, Inc. 11320 Watertown Plank Road, Wauwatosa, Wis. 53226-3413. This adhesive is a pressure sensitive linear SIS, styrene-isoprene-styrene, hotmelt adhesive. The adhesive is applied at a glue weight of 0.009 g/in2 using a Meltex EP34S spray application head. The temperature of the adhesive at the nozzle is 330 F. This spray application head is available from the Nordson Corporation, 2905 Pacific Drive, Norcross, Ga. 30071-1809. Once the glued is applied, a polyethylene film, 1.2 mil thickness, is adhered to the composite structure by placing the polyethylene in contact with the adhesively coated composite structure and applying pressure by rolling the sample with a hand roller similar to those used for wallpaper. Samples are then cut to a 2.54 cm (1 inch) width and 10.16 cm (4 inch) length with 1 inch of the length being the adhesively bonded area. At least 3 samples are prepared for both wet and dry bond. For the wet bond the adhesive end of the sample is placed in a petri dish filled with distilled water for 15 minutes. Immediately upon removal from the water the sample is tested as follows. Dry bond testing requires only the sample prep described previously and then testing as follows. The free, unbonded, ends of the sample are mounted in the clamps of the tester which are set 5.08 cm (2.0 in) apart. The tester is started and run at a cross-head speed of 50.8 cm/min (20.0 in/min). The computer starts picking up readings after the slack is removed, nominally a 5 gram pre-load. The sample is peeled completely, about 2.54 cm (1 inch) during which sufficient readings are taken to provide a representative average of the data. The peak load and average bond strength is given in N/cm. For samples that are peeled the entire 1 inch, the average bond strength is considered to be the bond strength. For samples that do not peel the entire 1 inch due to either bond conditions or failures in the substrates, the peak load is considered to be the bond strength.

Water Absorption is measured according to ASTM D570, which is hereby incorporated by reference.

Moisture Vapor Transmission Rate (MVTR) was determined by a method that is based in part on ASTM E96, which is hereby incorporated by reference, and is reported in $g/m^2/24$ hrs.

Figure 6:
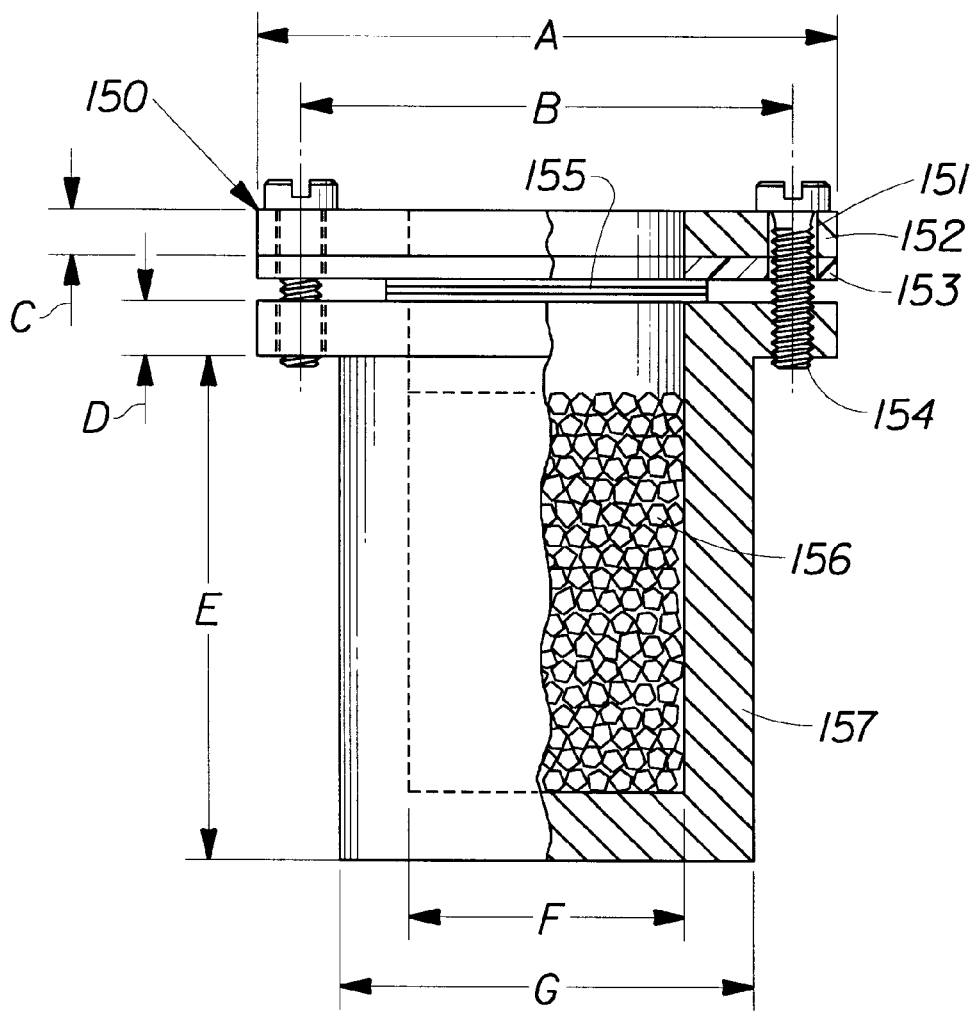
FIG. 6 is a simplified illustration of an apparatus used for measuring the moisture vapor transmission rate of a sheet material.

This method is referred to as the "dessicant method" for measuring moisture vapor transmission rate as set forth below. Briefly summarizing this method, a defined amount of desiccant ($CaCl_2$) is put into a flanged "cup" like container, see FIG. 6 shown with a partial cutaway. The sample 155 material is placed on the top of the container 157 and held securely by a retaining ring 152 and gasket 153. The assembly 150 is then weighed and recorded as the initial weight. The assembly is placed in a constant temperature (40° C.+/−3° C.) and humidity (75% RH+/−3%) chamber for five (5) hours. The assembly is then removed from the chamber, sealed to prevent further moisture intake, and allowed to equilibrate for at least 30 minutes at the temperature of the room where the balance is located. The amount of moisture absorbed by the $CaCl_2$ 156 is determined gravimetrically and used to estimate the moisture vapor transmission rate (MVTR) of the sample by weighing the assembly deducting the initial weight from the final assembly weight. The moisture vapor transmission rate (MVTR) is calculated and expressed in $g/m^2/24$ hr. using the formula below. Samples are assayed in triplicate. The reported MVTR is the average of the triplicate analyses, rounded to the nearest 100. The significance of differences in MVTR values found for different samples can be estimated based on the standard deviation of the triplicate assays for each sample.

Suitable Analytical Balances for performing the gravimetric measurements include a Mettler AE240 or equivalent (300 g capacity) or a Sartorius 2254S0002 or equivalent (1000 g capacity). A suitable sample holding assembly comprises a cup 157 and retaining ring 152 machined from Delrin® (such as that available from McMaster-Carr Catalog #8572K34) with a gasket 153 made of GC Septum Material (Alltech catalog #6528). The dimensions of the cup, retaining ring and gasket are as follows: the dimensions of the cup are A which corresponds to the retaining ring outer diameter and cup flange diameter is 63 mm, B is 55 mm, C which is the retaining ring thickness is 5 mm, D which is the flange thickness is 6 mm, E is the cup height and the dimension is 55 mm, F corresponds to the inner diameter of the cup and also the diameter of the opening in the retaining ring this dimension is 30 mm, G is the outer diameter of the cup which is 45 mm. The dessicant comprises $CaCl_2$ 156 for U-tubes, available from Wako Pure Chemical Industries, Ltd., Richmond, Va. Product # 030-00525. The plastic food wrap comprises Saran Wrap, available from Dow Chemical Company, or equivalent. A suitable environmental chamber is available from Electro-Tech Systems, Inc, ETS, model 506A or equivalent. The temperature controller is ETS model 513A or equivalent, the humidity controller is ETS model 514 or equivalent, the heating unit is a Marley Electric Heating Model 2512WC (400 watts) or equivalent, the humidifier is ETS model 5612B or equivalent.

The $CaCl_2$ can be used directly from a sealed bottle as long as the size of the lumps is such that they do not pass through a No. 10 sieve. Usually the top two-thirds of the bottle does not have to be seived. However, the bottom third contains fines that should be removed by sieving. The $CaCl_2$ can be used from a closed container without drying. It can be dried at 200° C. for 4 hours if required.

Representative samples should be obtained from the materials to be tested. Ideally, these samples should be taken from different areas of the material so as to represent any variations present. Three samples of each material are needed for this analysis.

Samples should be cut into rectangular pieces approximately 1.5"×2.5". If the samples are not uniform, clearly mark the area for which breathability is to be evaluated. If the samples are not bidirectional, clearly mark the side that is to be exposed to high humidity. For samples used in diapers and catamenials, this is usually the side that contacts the absorbent layer of the article or the wearer in the case of garments.

To begin a test session, (1) weigh approximately 15 grams of $CaCl_2$ 156 and place in the MVTR cup 157. Gently tap the cup 157 10 times on the bench top to distribute and lightly pack the $CaCl_2$. The $CaCl_2$ 156 should be level and about 1 cm from the top of the cup 157. Adjust the amount of CaCl2 until the 1 cm distance is achieved. Then (2) place the sample 155, with the high humidity side up (if required), over the opening in the top of the cup 157. Make sure that the sample overlaps the opening so that a good seal will be obtained. Next, (3) place the gasket material 153 and the retaining ring 152 on the top of the cup, aligning the screw holes 151 and checking to make sure that the sample has not moved. Tighten the screws 154 to securely fasten the retaining ring 152 and seal the sample to the top of the cup. Care should be taken to not over tighten the screws 154 as this leads to distortion of some samples. If distortion of the sample occurs, loosen the screws 154 and tighten again. Then (4) weigh the MVTR cup assembled in step 3. Record this weight as the initial weight. This process should be conducted in a relatively short time per cup, <2 minutes.

After weighing the assembly, (5) place the sample in the CT/CH chamber for 5.0 hours (to the nearest minute). When the time has elapsed, (6) remove the sample from the CT/CH chamber, tightly cover it with plastic wrap secured by a rubber band. Record the time of sample removal to within the nearest minute. Allow samples to equilibrate for at least 30 minutes at the temperature of the room where the balance is located. After equilibration, (7) remove the plastic wrap and rubber band and weigh the cup. Record this weight as the final weight.

The MVTR is then calculated in units of g $H_2O/24$ hr/m2 using the formula:

$$MVTR = \frac{(\text{final weight} - \text{initial weight}) \times 24.0}{\text{area of sample in meters} \times 5.0 \text{ (time in chamber)}}$$

where: 24.0 is used to convert the data to the 24 hour basis;

the area of sample is equal to the open area of the mouth of the cup; and 5.0 is the duration of the test in hours.

Calculate the average MVTR for each set of triplicate. Round the average MVTR for each sample set to the nearest 100. Report this value as the MVTR for the sample of material.

Figure 5:
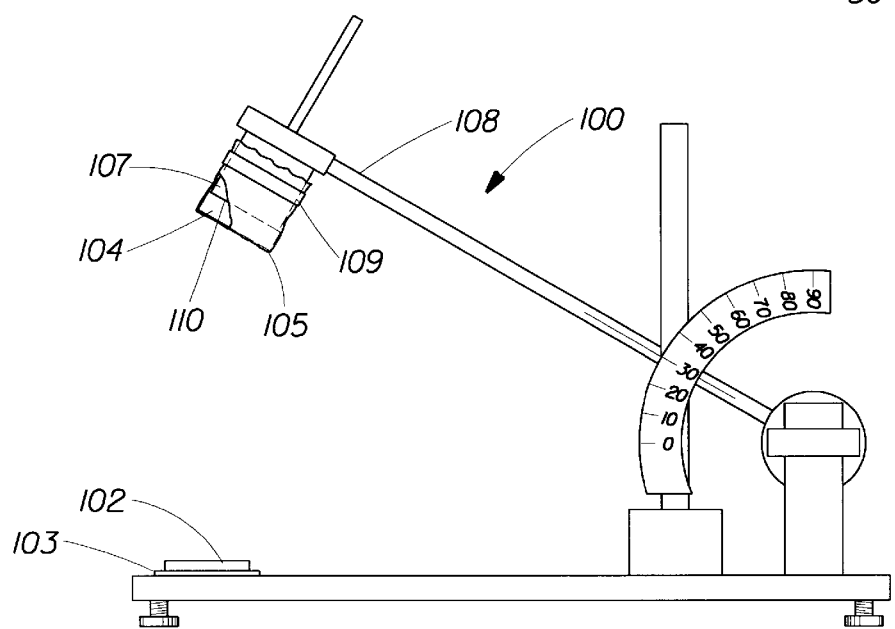
FIG. 5 is a simplified illustration of an apparatus used for measuring dynamic fluid transmission of a sheet material.

Dynamic Fluid Transmission is measured with the apparatus 100 shown in FIG. 5. According to this test, an absorption material 102 weighed to the nearest 0.0001 gram is placed directly on top of the energy absorbing impact pad 103. The absorption material 102 may comprise a No. 2 filter paper available from Whatman Laboratory Division, Distributed by VWR Scientific of Cleveland, Ohio. The absorption material should be able to absorb and retain the distilled water which passes through the sheet material being tested. The energy absorbing impact pad 103 is a carbon black filled cross linked rubber foam. The 5 inch by 5 inch square impact pad has a density of 0.1132 $g/cm^3$ and a thickness of 0.3125 inches. The impact pad 103 has a Durometer Value of A/30/15 according to ASTM 2240-91. A circular absorbent core material 104 measuring 0.0572 meters (2.25 inches) in diameter is weighed. The absorbent core material may comprise individualized, crosslinked wood pulp cellulosic fibers as described in U.S. Pat. No. 5,137,537 issued to Herron et al. on Aug. 11, 1992. The absorbent core material should be able to hold a sufficient amount of distilled water, e.g., at least about ten times its dry weight. The absorbent core has a basis weight of about 228 $g/m^2$. The absorbent core material is then is loaded with distilled water to about ten (10) times its dry weight.

A section of the backsheet material 105 to be tested is placed face down with the outside surface on a clean and dry tabletop. The loaded core material 104 is placed directly in the center of the backsheet material 105. The backsheet/core arrangement is then secured to the impact portion 107 of the impact arm 108 with a rubber band 109. The backsheet/core arrangement is positioned such that the core 104 is adjacent the bottom surface 110 of the impact portion 107. The impact arm 108 is raised to a desired impact angle to provide the desired impact energy. The impact arm 108 is dropped and the impact arm 108 is then immediately (about 1 second after impact) raised and the filter paper 102 is removed and placed on a digital scale. The mass of the wet filter paper is then recorded at the one minute mark. The dynamic fluid transmission value (DFTV) is calculated and expressed in $g/m^2$ using the following formula:

$$DFTV = \frac{\text{mass of the wet filter paper (grams)} - \text{mass of the dry filter paper (grams)}}{\text{impact area (m}^2\text{)}}$$

The impact area, expressed in $m^2$, is the area of the bottom surface 110 of the impact portion 107. The impact area is 0.00317 $m^2$. The absorbent core material 104 should have an area slightly larger than that of the impact area of the surface.

Gurley Hill Porosity is a measure of the barrier strength of the sheet material for gaseous materials. In particular, it is a measure of how long it takes for a volume of gas to pass through an area of material wherein a certain pressure gradient exists. Gurley-Hill porosity is measured in accordance with TAPPI T-460 om-88 using a Lorentzen & Wettre Model 121 D Densometer. This test measures the time of which 100 cubic centimeters of air is pushed through a one inch diameter sample under a pressure of approximately 4.9 inches of water. The result is expressed in seconds and is usually referred to as Gurley Seconds.

Bacterial Barrier for Sterile Packaging is measured according to ISO 11607 which states under section 4.2.3.2 that a material that is impermeable to air for one hour (according to an air porosity test) satisfies the standard's microbial barrier requirements. With regard to porous materials, section 4.2.3.3 of ISO 11607 states that there is no universally applicable method of demonstrating microbial barrier properties in porous materials, but notes that the microbial barrier properties of porous materials is typically conducted by challenging samples with an aerosol of bacterial spores or particulates under a set of test conditions which specify the flowrate through the material, microbial challenge to the sample, and duration of the test. One such recognized test is ASTM F 1608-95.

Viral Barrier properties were also measured according to ASTM F1671, which is hereby incorporated by reference. ASTM F1671 is a standard test method for measuring the resistance of materials used in protective clothing to penetration by blood-borne pathogens. According to this method, three samples of a sheet material being tested are challenged with $10^8$ Phi-X174 bacteriophage, similar in size to the Hepatitis C virus (0.028 microns) and with a surface tension adjusted to 0.042 N/m, at a pressure differential of 2 psi (13.8 kPa) for a 24 hour period. Penetration of the sample by viable viruses is determined using an assay procedure. The test results are reported in units of Plaque Forming Units per milliliter PFU/ml. A sample fails if any viral penetration is detected through any of the samples. A positive and negative control is run with each sample set. The positive control was a microporous membrane with a pore size of 0.04 microns which passed 600 PFU/ml. The negative control was a sheet of Mylar® film, which passed 0 PFU/ml.

Liquid Moisture Seepage is detected using a solution of 70 parts isopropyl alcohol, 30 parts water and 1 part red dye food color. According to this test, a sheet of a white absorbent blotting material measuring about 89 cm by 61 cm (35 in by 24 in) is placed on a flat surface and covered with a test sample of the same dimensions with the substrate side of the sample facing up. A 250 ml portion of the solution is poured on top of the test sample and covered with a template measuring about 46 ¾ cm by 46 ¾ cm (18 in by 18 in). A 4.5 kg (10 lb) weight is placed on top of the template for 10 minutes afterwhich the weight, template and test sample are removed from the white blotting paper. The paper is then inspected for ink spots to determine whether seepage occurred.

Film Components

The film compositions described in the examples below were prepared by dry blending one or more copolyether ester thermoplastic elastomers and titanium dioxide. The individual components in the film compositions were as follows:

Hytrel® 3548 is a copolyether ester thermoplastic elastomer sold by DuPont, and having a melting point of 156° C., a vicat softening temperature of 77° C., a shore hardness of 35D, and a water absorption of 5%.

Hytrel® 4778 is a copolyether ester thermoplastic elastomer sold by DuPont, and having a melting point of 208° C., a vicat softening temperature of 175° C., a shore hardness of 47D, and a water absorption of 2.3%.

Hytrel® 8206 is a copolyether ester thermoplastic elastomer sold by DuPont, and having a melting point of 200° C., a vicat softening temperature of 151° C., a shore hardness of 45D, and a water absorption of 30%.

Hytrel® 8171 is a copolyether ester thermoplastic elastomer sold by DuPont, and having a melting point of 150° C., a vicat softening temperature of 76° C., a shore hardness of 32D, and a water absorption of 54%.

$TiO_2$ Concentrate was a concentrate of 60% by weight particulate titanium dioxide pigment in high density polyethylene.

Examples 1–5

A copolyether ester film was adhesively laminated to a carded polypropylene nonwoven sheet with a basis weight of 27 g/m$^2$ (0.8 oz/yd$^2$) obtained for Fiberweb North America Inc. of Simpsonville, S.C. The nonwoven sheet was comprised of carded polypropylene staple fibers, with fiber lengths generally ranging between 2.5 cm and 7.5 cm, that were thermally bonded. The polypropylene fiber carded sheet had a tensile strength of 8.3 N/cm (4.73 lb/in) in the machine direction and 1.5 N/cm (0.86 lb/in) in the cross direction, and an elongation of 73% in the machine direction and 95% in the cross direction.

A pressure sensitive linear SIS hotmelt adhesive (H2031 from Ato Findley Adhesives, Inc. of Wauwatosa, Wis.) was applied to the nonwoven using a Series 6000 Melter and CF215 Applicator from the Nordson Corporation of Norcross Ga. The adhesive was applied in a substantially continuous filament in a dispersed spiral spray pattern that was 12 inches wide using 15 applicator modules that were 0.875 inches on center. The individual spiral patterns were applied edge to edge with no substantial overlap of the spiral patterns from the various applicator modules. The line speed of the nonwoven during adhesive application was 400 fpm (122 m/min). The basis weight of the applied adhesive was 2 mg/in$^2$ (3 g/m$^2$). The adhesive was covered with a release paper and the nonwoven coated with the adhesive was rolled up.

The nonwoven to which the adhesive and release paper had been applied was unrolled, the release paper was removed, and the adhesive coated side of the nonwoven was laminated with a polymer film comprised of 48% Hytrel® 8206 copolyether elastomer, 48% Hytrel® 8171 copolyether elastomer, and 4% titanium dioxide. The copolyether ester polymer was fed in pellet form into a 38 mm diameter screw extruder that was connected to a heated die. The polymer was melted and then fed to a 36 cm by 250 micron die opening in the heated die block. The polymer melt was extruded from the die opening and was coated on the polypropylene nonwoven sheet over the applied adhesive as described above with regard to FIG. 3. The film was joined to the fibrous nonwoven sheet in a nip that was spaced about 10 cm from the die opening. The nip was formed between a metal roll that faced the fibrous sheet and a rubber roll that faced the polymer melt.

In Examples 1–5 the line speed of the nonwoven was maintained at a constant 12 m/min (40 ft/min) and the film was extruded at constant rate (extruder speed of 12 rpm) in order to keep the thickness of the copolyether ester film constant. The polypropylene fiber sheet, the adhesive and the film were passed through the nip where the pressures on the nip were adjusted to form a variety of composite sheet structures. With the nip arrangement used in Examples 1–5, as shown in FIG. 3, cylinder pressures of 552 kPa (80 psi) correspond to a force of 172 N/linear cm along the length of the 20 inch long rolls; cylinder pressures of 414 kPa (60 psi) generate a force of 129 N/linear cm on the rolls; cylinder pressures of 276 kPa (40 psi) generate a force of 86 N/linear cm on the rolls; cylinder pressures of 138 kPa (20 psi) generate a force of 43 N/linear cm on the rolls; and cylinder pressures of 35 kPa (5 psi) generate a force of 11 N/linear cm on the rolls.

Other process conditions used in each example and the properties of the resulting composite sheets are set forth in Table 1 below.

TABLE 1

| EXAMPLE NUMBER | 1 (90J4) | 2 (90J3) | 3 (90J2) | 4 (90J5) | 5 (90J6) |
|---|---|---|---|---|---|
| Process Conditions | | | | | |
| Adhesive temperature (° C.) | ambient | ambient | ambient | ambient ambient | ambient |
| Adhesive application density (g/m$^2$) | 3 | 3 | 3 | 3 | 3 |
| Adhesive pattern | spiral | spiral | spiral | spiral | spiral |
| Linespeed (m/min) | 12 | 12 | 12 | 12 | 12 |
| Extrudeded melt temp (° C.) | 220 | 220 | 220 | 220 | 220 |
| Extruder speed 1 (RPM) | 12 | 12 | 12 | 12 | 12 |
| Die temperature (° C.) | 220 | 220 | 220 | 220 | 220 |
| Cylinder pressure (kpa) | 35 | 70 | 140 | 280 | 560 |
| Composite Properties | | | | | |
| Film Thickness (microns) | 25 | 25 | 25 | 24 | 24 |
| MVTR -(Desiccant Method) (g/m$^2$/day) | 2900 | 3200 | 2900 | 2800 | 3000 |

TABLE 1-continued

| EXAMPLE NUMBER | 1 (90J4) | 2 (90J3) | 3 (90J2) | 4 (90J5) | 5 (90J6) |
|---|---|---|---|---|---|
| Dynamic Impact (g/m$^2$ @ 2400 J/m$^2$) | 0.36 | 0.44 | 0.44 | 0.25 | 0.35 |
| Peel Strength (N/cm) | | | | | |
| MD | 0.95 | 1.04 | full | 1.03 | full |
| CD | 0.80 | 0.84 | full | 1.01 | full |

Examples 1–5 demonstrate that excellent peel strength can be obtained in a composite sheet at relatively low bonding pressures (Examples 1 and 2) when an adhesive is added between the film and the nonwoven. These examples also show that good moisture impact barrier properties can be obtained from a composite sheet with a thin moisture vapor permeable film when bonding pressures are kept low. Finally, these Examples support the belief that the film melt temperature is adequate to promote outstanding peel strength.

Examples 6–10

A copolyether ester film was adhesively laminated to the fibrous polypropylene nonwoven sheet of Examples 1–5. First, an adhesive was applied to the moving nonwoven sheet at three different adhesive basis weights using the adhesive coating process as described with respect to Examples 1–5 above. The adhesive was covered with a release paper and the nonwoven coated with the adhesive was rolled up.

The nonwoven to which the adhesive and release paper had been applied was unrolled, the release paper was removed, and the adhesive coated side of the nonwoven was laminated with a polymer film comprised of 48% Hytrel® 8206 copolyether elastomer, 48% Hytrel 8171 copolyether elastomer, and 4% titanium dioxide. The copolyether ester polymer was fed in pellet form into a 38 mm diameter screw extruder that was connected to a heated die. The polymer was melted and then fed to a 36 cm by 250 micron die opening in the heated die block. The polymer melt was extruded from the die opening and was coated on the polypropylene nonwoven sheet over the applied adhesive as described above with regard to FIG. 3. The film was joined to the fibrous nonwoven sheet in a nip that was spaced about 10 cm from the die opening. The nip was formed between a metal roll that faced the fibrous sheet and a rubber roll that faced the polymer melt.

In Examples 6–10, the line speed of the nonwoven and the speed at which the film was extruded were varied to produce films of different thicknesses. The nip arrangement was like that of Examples 1–5, and the pressure cylinders were maintained at a constant pressure of about 140 kPa (20 psi). The process conditions used in each example and the properties of the resulting composite sheets are set forth in Table 2 below.

TABLE 2

| EXAMPLE NUMBER | 6 (90J7) | 7 (90J8) | 8 (90J9) | 9 (90J2) | 10 (90J1) |
|---|---|---|---|---|---|
| Process Conditions | | | | | |
| Adhesive temperature (° C.) | Ambient | Ambient | Ambient | Ambient | Ambient |
| Adhesive application density (g/m$^2$) | 3 | 3 | 3 | 3 | 3 |
| Adhesive pattern | Spiral | Spiral | Spiral | Spiral | Spiral |
| Line speed (m/min) | 12 | 17 | 17 | 12 | 9 |
| Extrudeded melt temp (° C.) | 220 | 220 | 220 | 220 | 220 |
| Extruder speed 1 (RPM) | 12 | 12 | 6 | 12 | 16 |
| Die temperature (° C.) | 220 | 220 | 220 | 220 | 220 |
| Cylinder pressure (kpa) | 140 | 140 | 140 | 140 | 140 |
| Composite Properties | | | | | |
| Film Thickness (microns) | 17 | 12 | 7 | 25 | 37 |
| MVTR-(Desiccant Method) (g/m$^2$day) | 3300 | 3800 | 4800 | 2900 | 2600 |
| Dynamic Impact (g/m$^2$ @ 2400 J/m$^2$) | 0.25 | 0.33 | 0.33 | 0.44 | 0.25 |
| Peel Strength (N/cm) | | | | | |
| MD | full | full | full | full | 1.15 |
| CD | full | full | full | full | 0.97 |

Examples 6–10 demonstrate that the MVTR of the composite sheet can be improved by as much as 85% by reducing film thickness from 25 microns (Ex. 9) to 7 microns (Ex. 8). These Examples further show that this improved MVTR can be obtained without a significant loss in peel strength or dynamic impact barrier properties. These Examples support the belief that adhesive application prior to film extrusion is a viable process, and when combined with low bonding pressures, results in composites with films as thin as 7 microns that have adequate peel strength and dynamic impact barrier properties. These Examples also illustrate that application of the adhesive at the relatively low basis weight of about 3 g/m² is adequate to provide good peel strength.

Examples 11–16

A copolyether ester film was adhesively laminated to the fibrous polypropylene nonwoven sheet of Examples 1–5. First, an adhesive was applied to the moving nonwoven sheet at a coating density of 2 mg/in² (3 mg/cm²) as described with respect to Examples 1–5 above. The adhesive was covered with a release paper and the nonwoven coated with the adhesive was rolled up.

The nonwoven to which the adhesive and release paper had been applied was unrolled, the release paper was removed, and the adhesive coated side of the nonwoven was laminated with a polymer film comprised of 48% Hytrel® 8206 copolyether elastomer, 48% Hytrel® 8171 copolyether elastomer, and 4% titanium dioxide. The copolyether ester polymer was fed in pellet form into a 38 mm diameter screw extruder that was connected to a heated die. The polymer was melted and then fed to a 36 cm by 250 micron die opening in the heated die block. The polymer melt was extruded from the die opening and was coated on the polypropylene nonwoven sheet over the applied adhesive as described above with regard to FIG. 3. The film was joined to the fibrous nonwoven sheet in a nip that was spaced about 10 cm from the die opening. The nip arrangement was like that of Examples 1–5, and the pressure cylinders were maintained at a constant pressure of about 140 kPa (20 psi).

In Examples 11–13, the adhesive coating density was varied while other process conditions were kept constant. In Examples 14–18, the adhesive coating density was varied while a second set of process conditions were maintained. The process conditions used in each example and the properties of the resulting composite sheets are set forth in Table 3 below.

relatively high adhesive basis weights without causing a substantial reduction in moisture vapor transmission rates (Exs. 13 and 16). This data also suggests that the film melt temperature is high enough to soften the adhesive to promote good bonding.

Examples 17–21

A bi-layer copolyether ester polymer film was laminated to a nonwoven sheet comprised either of a polyester and polypropylene staple fiber blend or of 100% polyethylene staple fibers. No additional adhesive was used.

The nonwoven sheet material of Examples 17–20 was a 50/50 blend of polyester staple fiber (Dacron® Type 54 polyester fiber manufactured by DuPont) and polypropylene staple fibers (Danaklon Hy Comfort polypropylene fiber manufactured by Danaklon America, Inc. of Athens, Ga.). The polyester and polypropylene staple fibers had fiber lengths of about 40 mm and a denier of 2. The fibers were carded and thermobonded at 143° C. with a nip pressure of 40 daN/cm using a Kuester calender Hot-S-Roll. The nonwoven blend used in Examples 17–20 had basis weights ranging from 9.9 g/m² to 28.3 g/m².

The nonwoven sheet material of Example 21 was comprised solely of spunbonded polyethylene fiber with a basis weight 28.3 g/m² manufactured by Polybond Company of Waynesboro, Va.

The bi-layer copolyether ester film used in Examples 17–21 had a Film Layer 1 comprised of 100% Hytrel® 4778 that made up 17%, by weight of the film, and a Film Layer 2 comprised of a blend of 48% Hytrel® 8171, 46% Hytrel® 8206 and 6% $TiO_2$ that made up 83% of the film (percents are by weight). The components for Film Layer 1 were mixed and fed in pellet form into a 4 inch (10.2 cm) inch diameter screw extruder that was connected to a melt combining block. The components for Film Layer 2 were also mixed and fed in pellet form into a different 3 inch (7.6

TABLE 3

| EXAMPLE NUMBER | 11 (90L2) | 12 (90J2) | 13 (90K2) | 14 (90L4) | 15 (90J7) | 16 (90K3) |
|---|---|---|---|---|---|---|
| Process Conditions | | | | | | |
| Adhesive temperature (° C.) | Ambient | Ambient | Ambient | Ambient | Ambient | Ambient |
| Adhesive application density (g/m²) | 1.6 | 3 | 6.2 | 1.6 | 3 | 6.2 |
| Adhesive pattern | Spiral | Spiral | Spiral | Spiral | Spiral | Spiral |
| Line speed (m/min) | 12 | 12 | 12 | 12 | 12 | 12 |
| Extrudeded melt temp (° C.) | 220 | 220 | 220 | 220 | 220 | 220 |
| Extruder speed 1 (RPM) | 16 | 16 | 16 | 12 | 12 | 12 |
| Die temperature (° C.) | 220 | 220 | 220 | 220 | 220 | 220 |
| Cylinder pressure (kPa) | 140 | 140 | 140 | 140 | 140 | 140 |
| Composite Properties | | | | | | |
| Film Thickness (microns) | 26 | 25 | 30 | 23 | 17 | 24 |
| MVTR-(Desiccant Method) (g/m²/day) | 2800 | 2900 | 2400 | 3000 | 3300 | 3000 |
| Dynamic Impact (g/m² @ 2400 J/m²) | 0.03 | 0.44 | 0 | 0.13 | 0.25 | 0.11 |
| Peel Strength (N/cm) | | | | | | |
| MD | 0.59 | full | full | 0.49 | full | full |
| CD | 0.49 | full | full | 0.30 | full | full |

Examples 11–16 demonstrate that good peel strength can be obtained even at low adhesive basis weights (Exs. 11 and 14). These Examples also show that the open spiral pattern in which the adhesive is applied permits the application of cm) inch diameter screw extruder that was connected to the same melt combining block. The components for Film Layers 1 and 2 were each melted and extruded to the melt combining block. The two layer melt was then fed to a 762 microns by 102 cm die opening in a heated die block. A bicomponent film with Film Layer 1 and Film Layer 2 was extruded from the die opening and was coated on the polypropylene nonwoven sheet as shown in FIG. 4. The nonwoven sheet was spaced about 23 cm (9 in) below the opening of the die.

The nonwoven fiber sheet and the film were passed through a pair of nip rolls, as shown in FIG. 4, to form the composite sheet structure. The nip rolls were subjected to air cylinder pressures of 207 kPa (30 psi) and the rolls were maintained at ambient temperature. The process conditions used in each example and the properties of the resulting composite sheets are set forth in Table 4 below.

TABLE 4

| EXAMPLE NUMBER | 17 (3706) | 18 (3707) | 19 (3708) | 20 (3709) | 21 (3710) |
|---|---|---|---|---|---|
| Process Conditions | | | | | |
| Basis Weight - Nonwoven (g/m$^2$) | 28.3 | 19.8 | 14.2 | 9.9 | 28.3 |
| Line speed (m/min) | 36.6 | 39.6 | 42.7 | 45.7 | 36.6 |
| Extrudeded melt temp - Layer 1 (° C.) | 233 | 233 | 233 | 233 | 233 |
| Extruder speed - Layer 1 (RPM) | 40 | 40 | 40 | 40 | 40 |
| Extrudeded melt temp - Layer 2 (° C.) | 232 | 232 | 232 | 232 | 232 |
| Extruder speed - Layer 2 (RPM) | 33 | 33 | 33 | 33 | 33 |
| Die temperature (° C.) | 216 | 216 | 216 | 216 | 216 |
| Cylinder pressure (kPa) | 207 | 207 | 207 | 207 | 207 |
| Embossing roll temperature (° C.) | 43.3 | 43.3 | 43.3 | 43.3 | 43.3 |
| Water bath temperature (° C.) | 19.4 | 19.4 | 19.4 | 19.4 | 19.4 |
| Composite Properties | | | | | |
| Film Thickness (microns) | 22 | 22 | 22 | 22 | 22 |
| Composite Thickness (microns) | 188 | 150 | 107 | 89 | 371 |
| MVTR-(Desiccant Method) (g/m$^2$/day) | 3200 | 3400 | 3200 | 3100 | 3000 |
| Dynamic Impact (g/m$^2$ @ 2400 J/m$^2$) | 0.0 | 0.25 | 0.19 | 0.28 | 0.52 |
| Peel Strength (N/cm) | | | | | |
| MD | 0.98 | 1.08 | 0.97 | 0.74 | 0.09 |
| CD | 0.69 | 0.53 | 0.34 | 0.45 | 0.08 |
| Tensile Strength (N/cm) | | | | | |
| MD | 7.0 | 6.3 | 5.6 | — | — |
| CD | 1.6 | 1.3 | 1.1 | — | — |
| Elongation (%) | | | | | |
| MD | 24.0 | 28.7 | 27.6 | — | — |
| CD | 53.4 | 61.7 | 51.0 | — | — |
| Pinhole Seepage | 0 | 0 | 0 | 0 | 0 |
| Hydrostatic Head (cm) | 198 | 183 | 231 | 203 | 211 |
| Gurley Hill Air Porosity (sec) | >3600 | >3600 | >3600 | >3600 | >3600 |

Three samples of the composite sheet material (fibrous substrate and film without the polyethylene film) produced in Example 17 were tested according to the Viral Barrier test method described above. All three samples passed the Viral Barrier test (zero PFU/ml were detected after the 24 hour test period).

Examples 17–20 demonstrate that outstanding peel strength can be obtained at low bonding pressures, even in the absence of an adhesive. These Examples show that the presence of a limited amount of polyester in the fibrous substrate greatly enhances peel strength. These Examples also show that it is possible to achieve good peel strength and excellent dynamic impact barrier properties at the same time. Example 21 demonstrates that the lack of polyester results in low peel strength in the absence of an adhesive.

Examples 22–25

The film compositions used in Examples 22–25 had the following compositions:

| EXAMPLE | 22 (3644) | 23 (3645) | 24 (3646) | 25 (3643) |
|---|---|---|---|---|
| Film Layer 1 (wt. % of layer 1) | | | | |
| Hytrel ® 8206 (%) | — | 40 | — | — |
| Hytrel ® 4778 (%) | — | 60 | 100 | — |
| Hytrel ® 3548 (%) | 100 | — | — | — |

-continued

| EXAMPLE | 22 (3644) | 23 (3645) | 24 (3646) | 25 (3643) |
|---|---|---|---|---|
| Film Layer 2 (wt. % of Layer 2) | | | | |
| Hytrel ® 8171 (%) | 48 | 48 | 48 | 48 |
| Hytrel ® 8206 (%) | 46 | 46 | 46 | 46 |
| TiO$_2$ Concentrate (%) | 6 | 6 | 6 | 6 |
| Layer 1 (wt % of total film) | 17 | 17 | 17 | 0 |
| Layer 2 (wt % of total film) | 83 | 83 | 83 | 100 |

A polymer film comprised of the Film Layers 1 and 2 set forth above was extrusion coated on a fibrous polypropylene nonwoven sheet by the following process. The nonwoven sheet was the carded polypropylene sheet material described for Examples 1–5 above.

The components for Film Layer 1 were mixed and fed in pellet form into a 4 inch (10.2 cm) diameter screw extruder that was connected to a melt combining block. The components for Film Layer 2 were also mixed and fed in pellet form into a different 3 inch (7.6 cm) diameter screw extruder that was connected to the same melt combining block. The components for Film Layers 1 and 2 were melted and coextruded to the melt combining block. The two layer melt was then fed to a die opening (0.76 mm microns by 102 cm) in a heated die block. A bicomponent film with Film Layer 1 and Film Layer 2 was extruded from the die opening and was coated on the polypropylene nonwoven sheet without the application of an adhesive. The polypropylene fiber sheet was spaced 22.9 cm (9 in) below the opening of the die.

The polypropylene fiber sheet, the adhesive and the film were passed through a pair of nip rolls, as shown in FIG. 4. The nip rolls were subjected to cylinder pressures of 689 kPa (100 psi). The process conditions used in each example and the properties of the resulting composite sheets are set forth in Table 5 below.

The film side of the composite sheet was subsequently glued to a polyethylene film to determine whether the composite sheet would remain bonded to such films under conditions that might be encountered in an absorbent article. A pressure sensitive linear SIS hotmelt adhesive (hotmelt adhesive H2031 from Ato Findley Adhesives, Inc., of Wauwatosa, Wis.) was applied to the film side of the composite sheet at an adhesive basis weight of 0.009 g/in$^2$ (13.95 g/m$^2$) using a Meltex EP34s spray application head available from Nordson Corporation. The temperature of the adhesive leaving the spray head was 166° C. A sheet of polyethylene film with a thickness of 1.2 mil (30.5 microns) was pressed against the side of the composite sheet to which the adhesive was applied using a hand roller. The dry and wet strength of the bond between the composite sheet and the polyethylene film was measured and is reported in Table 5 below.

TABLE 5

| EXAMPLE NUMBER | 22 (3644) | 23 (3645) | 24 (3646) | 25 (3643) |
|---|---|---|---|---|
| Process Conditions | | | | |
| Line speed (m/min) | 27.4 | 27.4 | 40.8 | 27.4 |
| Extrudeded melt temp - Layer 1 (° C.) | 243 | 243 | 243 | 243 |
| Extruder speed - Layer 1 (RPM) | 20 | 20 | 37 | 80 |
| Extrudeded melt temp - Layer 2 (° C.) | 260 | 260 | 260 | — |
| Extruder speed - Layer 2 (RPM) | 21 | 21 | 27 | — |
| Die temperature (° C.) | 243 | 243 | 243 | 243 |
| Cylinder pressure (kPa) | 689 | 689 | 689 | 689 |
| Embossing roll temperature (° C.) | 60 | 60 | 60 | 60 |
| Water bath temperature (° C.) | 49 | 49 | 49 | 49 |
| Composite Properties | | | | |
| Film Thickness (microns) | 23 | 23 | 23 | 23 |
| MVTR-(Desiccant Method) (g/m$^2$/day) | 3850 | 3150 | 2950 | 3600 |
| Peel Strength (N/cm) | | | | |
| MD | 0.36 | 0.43 | 0.64 | 0.25 |
| CD | 0.25 | 0.46 | 0.51 | 0.20 |
| Tensile Strength (N/cm) | | | | |
| MD | 12.4 | 12.4 | 13.1 | — |
| CD | 2.3 | 2.4 | 2.4 | — |
| Elongation (%) | | | | |
| MD | 81 | 86 | 88 | — |
| CD | 105 | 107 | 105 | — |
| Gurley Hill Air Porosity (sec) | >3600 sec | >3600 sec | >3600 sec | >3600 sec |
| Hydrostatic Head (cm) | 66 | 46 | 56 | 43 |
| Article Construction | | | | |
| Dry Bond Strength (g/cm) | 156.7 | 122.0 | 224.4 | 112.6 |
| Wet Bond Strength (g/cm) | 4.3 | 10.2 | 170.5 | 1.6 |

Examples 22–25 demonstrate that changes in the composition of a two layer moisture vapor permeable has a substantial impact on the MVTR of the composite sheet. These Examples also show that a polyethylene film can be bonded to the film layer of the composite sheet with conventional hot melt adhesives. Finally, these Examples show that by making the outer film layer from a more hydrophobic polyether ester elastomer, good wet bond strength can be obtained (Example 24). Examples 22–25 illustrate that the polypropylene based fibrous substrate requires >3 times the bonding pressure relative to examples 17–20 which comprised polyester and polypropylene fiber blends. The compatible polyester fibers allow significantly lower pressures to be used while achieving a significant improvement in peel strength versus Examples 22–25. Examples 22–25, even though they were bonded at higher pressure, resulted in peel strengths that were nominally 50% of the peel achieved with examples 17–20. In order for Examples 22–25 to achieve the level of bonding seen with Examples 17–20, higher bonding pressure is required. Because Examples 22–25 already incorporate higher melt temperature which is amenable to bonding, but reduces the viscosity of the polymer, it is very likely that increasing the bonding strength will result in an increase in pinholes and impact related leakage.

Examples 26–29

A copolyether ester film was extrusion coated directly onto a number of different fibrous nonwoven sheets without the use of a separate adhesive. In Examples 26–29, the composition of the nonwoven sheet had a basis weight of 14.2 g/m² (0.5 oz/m²), and had one of the following compositions: Composition A: a 50/50 blend of polyester staple fiber (Dacron® Type 54 polyester fiber manufactured by DuPont) and polypropylene staple fibers (Danaklon Hy Comfort polypropylene fiber manufactured by Danaklon America, Inc. of Athens, Ga.). The polyester and polypropylene staple fibers had fiber lengths of about 40 mm and a denier of 2. The fibers were carded and thermobonded on a B.F. Perkins Calender Bonder at a temperature of 130°–145° C. with a very light nip pressure.

Composition B: a 50/50 blend of polyester and polypropylene fibers like Composition A with the exception the Dacron® Type 54 polyester fiber was replaced with shaped polyester fibers having a scalloped-oval cross-section, as described in U.S. Pat. No. 3,914,488, and having an average fiber length of 40 mm and a denier of 1.4. The fibers were carded and thermobonded on a B.F. Perkins Calender Bonder at a temperature of 130°–145° C. with a very light nip pressure.

Composition C: a blend of 75% polyester staple fiber (Dacron® Type 54 polyester fiber manufactured by DuPont) and 25% polypropylene staple fibers (Danaklon Hy Comfort polypropylene fiber manufactured by Danaklon America, Inc. of Athens, Ga.). The polyester and polypropylene staple fibers had fiber lengths of about 40 mm and a denier of 2. The fibers were carded and thermobonded on a B.F. Perkins Calender Bonder at a temperature of 130°–145° C. with a very light nip pressure.

Composition D: a 75/25 blend of polyester and polypropylene fibers like Composition C with the exception the Dacron® Type 54 polyester fiber was replaced with shaped polyester fibers having a scalloped-oval cross-section, as described in U.S. Pat. No. 3,914,488, and having an average fiber length of 40 mm and a denier of 1.4. The fibers were carded and thermobonded on a B.F. Perkins Calender Bonder at a temperature of 130°–145° C. with a very light nip pressure.

The nonwoven was laminated with a polymer film comprised of 48% Hytrel® 8206 copolyether elastomer, 48% Hytrel®) 8171 copolyether elastomer, and 4% titanium dioxide. The copolyether ester polymer was fed in pellet form into a 38 mm diameter screw extruder that was connected to a heated die. The polymer was melted and then fed to a 36 cm by 250 micron die opening in the heated die block. The polymer melt was extruded from the die opening and was coated on the polypropylene nonwoven sheet as shown in FIG. 3. The film was joined to the fibrous nonwoven sheet in a nip that was spaced about 10 cm from the die opening. The nip arrangement was like that of Examples 1–5, and the pressure cylinders were maintained at a constant pressure of about 140 kPa (20 psi). The process conditions used in each example and the properties of the resulting composite sheets are set forth in Table 6 below.

TABLE 6

| EXAMPLE NUMBER | 26 (90E3) | 27 (90F8) | 28 (90G12) | 29 (90G13) |
|---|---|---|---|---|
| Nonwoven Composition | A | B | C | D |
| Process Conditions | | | | |
| Nonwoven speed (m/min) | 12 | 12 | 12 | 12 |
| Extrudeded melt temp (° C.) | 220 | 220 | 220 | 220 |
| Extruder speed (RPM) | | | | |
| Die temperature (° C.) | 220 | 220 | 220 | 220 |
| Cylinder pressure (kPa) | 140 | 140 | 140 | 140 |
| Composite Properties | | | | |
| Film Thickness (microns) | 26 | 24 | 25 | 27 |
| Composite Thickness (mm) | | | | |
| MVTR-(Desiccant Method) (g/m²/day) | 2600 | 3100 | 2400 | 2900 |
| Dynamic Impact (g/m² @ 2400 J/m²) | 0.19 | | 0.00 | 0.00 |
| Peel Strength (N/cm) | | | | |
| MD | 0.61 | 0.88 | weak | 0.63 |
| CD | 0.24 | 0.20 | weak | 0.11 |

Examples 26–29 illustrate the impact of the use of shaped fibers in the fibrous substrate of the composite structure. Without wishing to be bound by theory, it is believed that the shaped fibers, when brought into contact with the film melt, increase the surface area of the film, thereby increasing the flux of vapor through the composite structure. The types of non-porous, liquid impermeable, vapor permeable films transmit vapor by first absorption, then diffusion and finally evaporation. Increasing the surface area for the evaporation step will increase the vapor transmission.

Examples 30–41

Copolyether ester films were extrusion coated directly onto four different fibrous nonwoven sheets without the use of a separate adhesive. The four nonwovens were comprised of various combinations of polypropylene fibers and polyester fibers. The nonwoven sheets used in Examples 30–41 had one of the following compositions:

Composition E: carded polypropylene fibers thermally bonded as fully described in Examples 1–5

Composition F: blend of 26% polyethylene terepthalate polyester fibers (Dacron® Type 54 polyester fiber manufactured by DuPont) and 74% polypropylene fibers. blend of polyester staple fiber (Danaklon Hy Comfort polypropylene fiber manufactured by Danaklon America, Inc. of Athens, Ga.). The polyester and polypropylene staple fibers had fiber lengths of about 40 mm and a denier of 2. The fibers were carded and thermobonded on a B.F. Perkins Calender Bonder at a temperature of 130°–145° C. with a very light nip pressure.

Composition G: a 50/50 blend of polyethylene terepthalate polyester fibers and polypropylene staple fibers identical to Composition A described above with respect to Examples 26–29.

Composition H: 100% polyethylene terepthalate polyester fibers with a fiber lengths of about 40 mm and a denier of 2. The fibers were carded and thermobonded on a B.F. Perkins Calender Bonder at a temperature of 130°–145° C. with a very light nip pressure.

The two films used were as follows:

Film 1 was a single layer film comprised of 47% Hytrel® 8206 copolyether elastomer, 47% Hytrel® 8171 copolyether elastomer, and 6% titanium dioxide.

Film 2 was a two layer film in which Layer 1 was comprised of the blend of Film 1, and Layer 2 was comprised of 100% Hytrel® 8206 copolyether elastomer.

The copolyether ester polymer was fed in pellet form into a 38 mm diameter screw extruder that was connected to a heated die. The polymer was melted and then fed to a 36 cm by 250 micron die opening in the heated die block. The polymer melt was extruded from the die opening and was extrusion coated on the nonwoven sheet without the application of an adhesive. The film was joined to the fibrous nonwoven sheet in a nip that was spaced about 10 cm from the die opening. The nip arrangement was like that of Examples 1–5, and the pressure cylinders were maintained at a constant pressure of about 140 kPa (20 psi).

The process conditions used in each example and the properties of the resulting composite sheets are set forth in Table 7 below.

TABLE 7

| EXAMPLE NUMBER | 30 (130T1) | 31 (130T4) | 32 (130T3) | 33 (130T2) |
|---|---|---|---|---|
| Nonwoven Composition | E | F | G | H |
| Film Composition | 1 | 1 | 1 | 1 |
| Process Conditions | | | | |
| Line speed (m/min) | 12.2 | 12.2 | 12.2 | 12.2 |
| Extrudeded melt temp (° C.) | 220 | 220 | 220 | 220 |
| Extruder speed (RPM) | 20 | 20 | 20 | 20 |
| Die temperature (° C.) | 220 | 220 | 220 | 220 |
| Cylinder pressure (kPa) | 138 | 138 | 138 | 138 |
| Composite Properties | | | | |
| Film Thickness (microns) | 25 | 25 | 25 | 25 |
| MVTR-(Desiccant Method) (g/m²/day) | 4000 | 3700 | 3600 | 2900 |

| EXAMPLE NUMBER | 34 (130V1) | 35 (130V4) | 36 (130V3) | 37 (130V2) |
|---|---|---|---|---|
| Nonwoven Composition | E | F | G | H |
| Film Composition | 1 | 1 | 1 | 1 |
| Process Conditions | | | | |
| Line speed (m/min) | 21 | 21 | 21 | 21 |
| Extrudeded melt temp (° C.) | 220 | 220 | 220 | 220 |
| Extruder speed (RPM) | 20 | 20 | 20 | 20 |
| Die temperature (° C.) | 220 | 220 | 220 | 220 |
| Cylinder pressure (kPa) | 138 | 138 | 138 | 138 |
| Composite Properties | | | | |
| Film Thickness (microns) | 12 | 12 | 12 | 12 |
| MVTR-(Desiccant Method) (g/m²/day) | 4400 | 4200 | 4500 | 3500 |

| EXAMPLE NUMBER | 38 (130A1) | 39 (130A4) | 40 (130A3) | 41 (130A2) |
|---|---|---|---|---|
| Nonwoven Composition | E | F | G | H |
| Film Composition | 2 | 2 | 2 | 2 |
| Process Conditions | | | | |
| Line speed (m/min) | 10.5 | 10.5 | 10.5 | 10.5 |
| Extrudeded melt temp - layer 1 (° C.) | 220 | 220 | 220 | 220 |
| Extrudeded melt temp - layer 2 (° C.) | 220 | 220 | 220 | 220 |
| Extruder speed - layer 1 (RPM) | 15 | 15 | 15 | 15 |
| Extruder speed - layer2 (RPM) | 12 | 12 | 12 | 12 |
| Die temperature (° C.) | 220 | 220 | 220 | 220 |
| Cylinder pressure (kPa) | 138 | 138 | 138 | 138 |
| Composite Properties | | | | |
| Film Thickness (microns) | 25 | 25 | 25 | 25 |
| MVTR-(Desiccant Method) (g/m²/day) | 3500 | 2500 | 2900 | 1600 |

Examples 17–20 illustrated the positive impact of polyester, compatible, fiber inclusion in the fibrous substrate upon the peel strength. Examples 30–41 illustrate that the inclusion of polyester fibers can also have a negative affect on MVTR. This negative affect is associated with the increase in fiber to film bonds associated with the polyester, compatible, fibers. The data in Table 7 shows that the composite structure comprising a polypropylene only fibrous substrate has a higher MVTR than all but one of the other Examples, Example 36. The Table 7 data also shows that the composite structures with the blended, 50% polyester and 50% polypropylene, fibrous substrates are substantially higher in MVTR than the composite structure comprising a 100% polyester fibrous substrate.

Example 42

A sample of Exxon Exxair XFB-100W microporous film, available from Exxon Chemical Company of Buffalo Grove, Ill., USA, was laminated to a moisture vapor permeable film comprised of 100% Hytrel® 8171 copolyether elastomer. The microporous film was coated with the pressure sensitive linear SIS hotmelt adhesive described in Examples 1–5 above at an adhesive basis weight of 0.001 g/in². The moisture vapor permeable film, which had been melt cast on a release paper with a thickness of 13 microns, was bonded to the adhesive on the microporous film.

The microporous sheet, the moisture vapor permeable film, and the composite of the two had the following properties.

| | MVTR (g/m²/day) (Dessicant Method) | Dynamic Impact (g/m² @ 2400 joules) |
|---|---|---|
| Microporous Film | 4,600 | 1.26 |
| Hytrel ® Film | 3,900 | 0.00 |
| Composite | 3,500 | 0.23 |

This Example shows the addition of a moisture vapor permeable film to a microporous film significantly reduces moisture impact related leakage from a microporous film.

Comparative Example 1

A sample of Exxon Exxair XFB-100W microporous film, available from Exxon Chemical Company of Buffalo Grove, Ill., USA, was tested for moisture vapor transmission rate, dynamic fluid transmission, microbial barrier for sterile packaging, and liquid moisture seepage. The properties measured were as follows:

| | |
|---|---|
| MVTR (g/m²/24 hr) | 4000 |
| Dynamic Impact (g/m² @ 2400 J/m²) | 0.97 |
| Microbial Barrier | Bacillus subtilis bacteria passage recorded in six of six samples tested after 15 minute exposure. (38.6 cm Hg vacuum; 2.8 l/min flow rate) |
| Moisture Seepage | Dye apparent on blotter indicating passage of liquid. |

REPRESENTATIVE ABSORBENT ARTICLES

Figure 7:
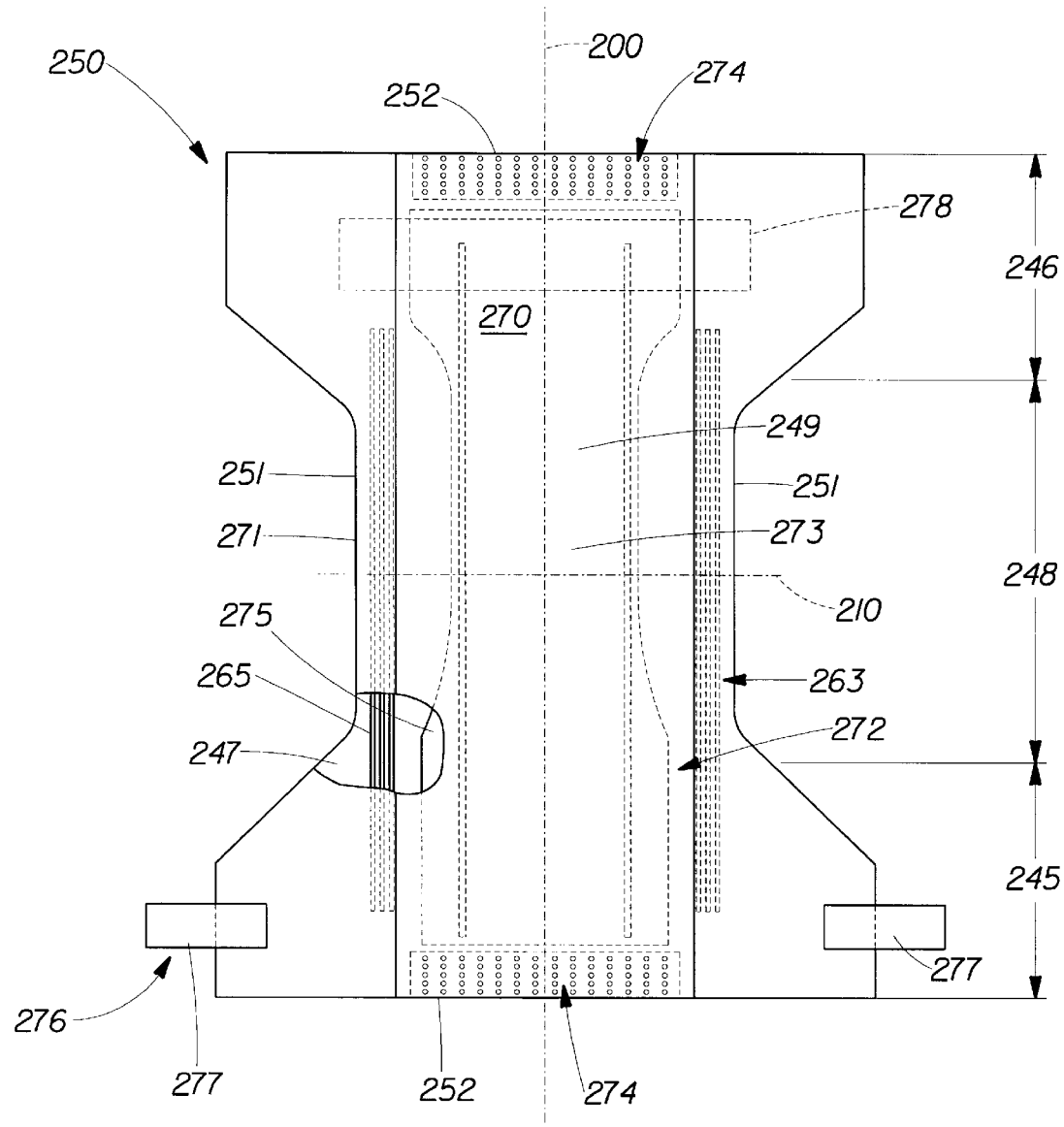
FIG. 7 is a plan view of a disposable diaper embodiment of the present invention having portions cut away to reveal underlying structure, as viewed from the inner surface of the diaper.

A preferred embodiment of an absorbent article incorporating the composite sheet of the present invention is the diaper 250, shown in FIG. 7. As used herein, the term "diaper" refers to an absorbent article generally worn by infants and incontinent persons that is worn about the lower torso of the wearer. FIG. 7 is a plan view of the diaper 250 of the present invention in its flat-out, uncontracted state (i.e., with elastic induced contraction pulled out) with portions of the structure being cut-away to more clearly show the construction of the diaper 250. As shown in FIG. 7, the diaper 250 preferably comprises a containment assembly 270 comprising a topsheet 249; a backsheet 247 joined to the topsheet; and an absorbent core 275 positioned between the topsheet 249 and the backsheet 247. The absorbent core 275 has a pair of opposing longitudinal edges, an inner surface and an outer surface. The diaper preferably further comprises elastic leg features 272; elastic waist features 274; and a fastening system 276 preferably comprising a pair of securement members 277 and a landing member 278.

The diaper 250 is shown in FIG. 7 with the portion of the diaper 250 which faces the wearer, the inner surface 273, facing the viewer. The diaper 250 is shown in FIG. 7 to have an inner surface 273 (facing the viewer in FIG. 7), an outer surface 271 opposed to the inner surface 273, a rear or back waist region 245, a front waist region 246 opposed to the rear waist region 245, a crotch region 248 positioned between the rear waist region 245 and the front waist region 246, and a periphery which is defined by the outer perimeter or edges of the diaper 250 in which the longitudinal or side edges are designated 251 and the end edges are designated 252. The inner surface 273 of the diaper 250 comprises that portion of the diaper 250 which is positioned adjacent to the wearer's body during use (i.e., the inner surface 273 generally is formed by at least a portion of the topsheet 249 and other components joined to the topsheet 249). The outer surface 271 comprises that portion of the diaper 250 which is positioned away from the wearer's body (i.e., the outer surface 271 is generally formed by at least a portion of the backsheet 247 and other components joined to the backsheet 247). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 245 and the front waist region 246 extend from the end edges 252 of the periphery to the crotch region 248.

The diaper 250 also has two centerlines, a longitudinal centerline 200 and a transverse centerline 210. The term "longitudinal", as used herein, refers to a line, axis, or direction in the plane of the diaper 250 that is generally aligned with (e.g. approximately parallel with) a vertical plane which bisects a standing wearer into left and right halves when the diaper 250 is worn. The terms "transverse" and "lateral", as used herein, are interchangeable and refer to a line, axis or direction which lies within the plane of the diaper that is generally perpendicular to the longitudinal direction.

Figure 8:
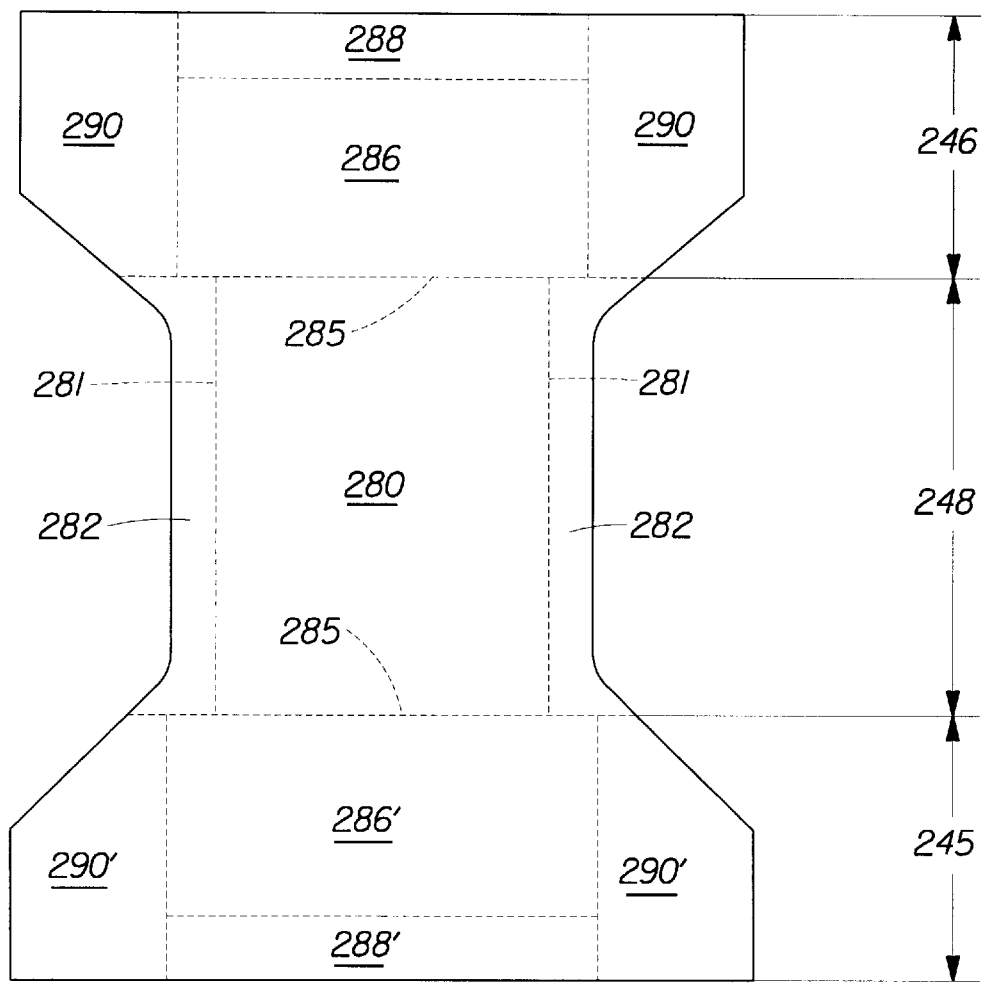
FIG. 8 is a simplified plan view of the disposable diaper of the present invention in its flat uncontracted condition showing the various panels or zones of the diaper.

FIG. 8 shows a simplified plan view of the diaper 250 of FIG. 7 depicting the various panels and their positioning with respect to each other. The term "panel" is used herein to denote an area or element of the diaper. (While a panel is typically a distinct area or element, a panel may coincide (functionally correspond) somewhat with an adjacent panel.) The diaper 250 has a crotch region 248 comprising a main panel 280 and a pair of leg panels 282; a front waist region 246 comprising a central panel comprising a medial panel 286 and a waistband panel 288, and side panels 290; and a rear waist region 245 comprising a central panel comprising a medial panel 286' and a waistband panel 288', and side panels 290'. The main panel 280 is the portion of the diaper 250 from which the other panels emanate. The absorbent core is generally positioned within the main panel 280 since exudates are typically discharged in this region of the diaper although the absorbent core will also likely extend into the medial panels 286 and 286'. A leg panel 282 extends generally laterally outwardly from and along each side edge 281 of the main panel 280. Each leg panel 282 generally forms at least a portion of the elastic leg feature. In the front waist region 246, the medial panel 286 of the central panel extends generally longitudinally outwardly from and along the lateral edge 285 of the main panel 280. The waistband panel 288 extends generally longitudinally outwardly from and along the medial panel 286. The side panels 290 each extend generally laterally outwardly from and along the central panel. In the rear waist region 245, the medial panel 286' of the central panel extends generally longitudinally outwardly from and along the lateral edge 285 of the main panel 280. The waistband panel 288' extends generally longitudinally outwardly from and along the medial panel 286'. The side panels 290' each extend generally laterally outwardly from and along the central panel.

Referring again to FIG. 7, the containment assembly 270 of the diaper 250 is shown as comprising the main body (chassis) of the diaper 250. The containment assembly 270 preferably comprises a topsheet 249, a backsheet 247 and an absorbent core 275 having a pair of opposing longitudinal edges, an inner surface, an outer surface. The inner surface of the absorbent core generally faces the body of the wearer while the outer surface generally faces away from the body of the wearer. When the absorbent article comprises a separate holder and a liner, the containment assembly 270 generally comprises the holder and the liner (i.e., the containment assembly 270 comprises one or more layers of material to define the holder while the liner comprises an absorbent composite such as a topsheet, a backsheet, and an absorbent core.) For unitary absorbent articles, the containment assembly 270 preferably comprises the topsheet 249, the backsheet 247 and the absorbent core 275 of the diaper with other features added to form the composite diaper structure.

FIG. 7 shows a preferred embodiment of the containment assembly 270 in which the topsheet 249 and the backsheet 247 have length and width dimensions generally larger than those of the absorbent core 275. The topsheet 249 and the backsheet 247 extend beyond the edges of the absorbent core 275 to thereby form the periphery of the diaper 250. While the topsheet 249, the backsheet 247, and the absorbent core 275 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; and U.S. Pat. No. 5,385,500 entitled "Absorbent Articles Providing Sustained Dynamic Fit" which issued to LaVon et al., on Oct. 25, 1994; each of which is incorporated herein by reference.

In the embodiment shown in FIG. 7, the backsheet 247 preferably comprises a continuous sheet or layer which defines the front waist region 246, the rear waist region 245, and the crotch region 248. As used herein, the term "layer" does not necessarily limit the element to a single strata of material in that a layer may actually comprise laminates or combinations of sheets or webs of the requisite types of materials. The backsheet 247 has an inner surface and an opposed outer surface. The inner surface is that portion of the backsheet 247 which is positioned adjacent the absorbent core. The outer surface of the backsheet 247 corresponds to the outer surface 271 of the diaper 250. Since the backsheet 247 preferably defines the front waist region 246, the rear waist 245, and the crotch region 248, the backsheet 247 also has corresponding regions and panels as previously defined.

(For simplicity, these regions and panels are denoted in the drawings by the same reference numerals as the corresponding diaper regions and panels as shown in FIG. 8.)

In the embodiment shown in FIG. 8, the absorbent core is positioned in the main panel 280, since exudates are typically discharged in this region and extends into the medial panels 286 and 286'. In the embodiment shown in FIG. 8, the absorbent core does not extend into the leg panels 282, the waistband panels 288 and 288', or the side panels 290 and 290'. In other embodiments, the absorbent core may extend into all or some of the leg panels 282, the waistband panels 288 and 288', and the side panels 290 and 290'.

The backsheet 247 of the present invention is that portion of the diaper 250 which is generally positioned away from the wearer's skin and which prevents the exudates absorbed and contained in the absorbent core 275 from wetting articles which contact the diaper 250 such as bedsheets and undergarments. Thus, the backsheet 247 is substantially impervious to fluids (e.g., urine). In addition to being fluid impervious, the backsheet 247 is also highly permeable to moisture vapor. For disposable diapers, moisture vapor permeability has been found to be critical to comfort related performance of absorbent articles. When an absorbent article comprised of non-breathable material is positioned on a wearer, the skin is occluded by the materials making up the absorbent article. This occlusion of the skin prevents escape of moisture vapor or evaporation and the resulting cooling of the occluded area. The resultant increase in perspiration in conjunction with fluid loading raises the relative humidity of air inside of the absorbent article resulting in reduced comfort for the wearer and perceived negative benefits by care givers. In order to reduce humidity and heat buildup within the disposable diaper, it has been found that at least a portion of the backsheet 247, and more preferably the entire backsheet 247, should have a moisture vapor transmission rate of at least about 1500 $g/m^2/24$ hr., and preferably at least about 3000 $g/m^2/24$ hr, and even more preferably at least about 4500 $g/m^2/24$ hr. As discussed above, the composite sheet 10 of the present invention has an ideal moisture vapor transmission rate for use as a backsheet in a disposable absorbent article, such as the disposable diaper 250 of FIG. 7. For such an application, the composite sheet 10 is employed with the film layer 12 forming the inner or core-facing portion of the backsheet and the substrate 14 forming the outer or garment-facing portion of the backsheet.

The backsheet 247 comprised of the composite sheet 10 is preferably positioned adjacent the outer surface of the absorbent core 275 and may be joined thereto by any suitable attachment means known in the art for bonding such materials. For example, the backsheet 247 may be secured to the absorbent core 275 by a uniform continuous layer of adhesive, a patterned layer of adhesive, or an array of separate lines, spirals, or spots of adhesive. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

In terms of approaches to bond the composite sheet material to other components of an absorbent article, and more particularly to bond the moisture vapor permeable, liquid impermeable film layer of the composite sheet to other components, it has been observed that only certain methods of bonding will form bonds of sufficient strength to survive forces encountered in normal use particularly after the film layer has been subjected to fluid contact and has absorbed fluid. Without wishing to be bound by theory it is presently believed that the film layers of interest in accordance with the present invention provide the desired superior performance properties in terms of moisture vapor transmission due to their comparatively high moisture content under in-use conditions. This comparatively high moisture content, however, is presently believed to have negative implications on the bond strength of the bond between certain conventional hot melt adhesives and the film layer.

One approach which has proven satisfactory is to utilize a polyurethanebased adhesive in accordance with the conventional adhesive application techniques and equipment generally well known in the art, such as described above. Another approach, which is presently preferred, is to utilize the multiple layer, co-extruded film layer described above with reference to the aforementioned and incorporated U.S. Pat. No. 4,725,481 to Ostapchenko. Ostapchenko discloses a bi-layer film in a composite film/nonwoven structure wherein the hydrophobic layer is oriented next to the fibrous layer. In utilizing this multiple layer film approach in accordance with the present invention, the multiple layer film structure (in a bi-layer execution) is extruded onto the fibrous substrate material with the comparatively more hydrophobic elastomer layer facing outwardly from the substrate and the comparatively more hydrophilic elastomer layer facing toward the substrate. Typically, for a given thickness the hydrophobic elastomer layer exhibits a lower MVTR performance than the hydrophilic elastomer layer due to its comparatively lower moisture content under in-use conditions. However, when employed in a comparatively thin layer, the effect of the hydrophobic lower moisture content film layer does not signficantly diminish the MVTR performance of the overall composite sheet. Due to the comparatively low moisture content of the hydrophobic elastomer layer, conventional hot melt adhesives and bonding techniques may be utilized to successfully form bonds of adequate strength between the composite sheet and other components of the absorbent article even when the film has been wetted. Accordingly, by utilizing a co-extruded, multiple layer, multi-chemistry film layer a composite sheet can be provided that exhibits both the desired performance properties for the composite sheet of the present invention and can be bonded to other components of absorbent articles via conventional adhesive bonding techniques. (See Examples 36–39 below.)

Quite unexpectedly, additional performance benefits have been discovered through the use of multiple layer films in composite sheets used in constructing absorbent articles such as diaper 250. More particularly, the use of a multiple layer film comprising a three-layer structure with a hydrophobic elastomer layer on both facing surfaces surrounding a hydrophilic elastomer layer is believed to deliver improved tactile qualities when extruded onto a fibrous substrate to form a composite sheet. Again without wishing to be bound by theory, it is believed that the comparatively lower moisture content of the hydrophobic film layers results in a drier tactile impression when the fibrous substrate layer is touched or palpated, particularly when the fibrous substrate layer is comparatively thin. Such a multiple layer (tri-layer) embodiment of a composite sheet material would therefore provide both improved bondability with conventional adhesive techniques and an improved tactile impression from the side of the fibrous substrate layer. Optionally, as discussed above, truly dual-sided configurations could be constructed analogously to FIG. 2 wherein the multiple layer/tri-layer film structure is faced on both sides with a fibrous substrate material to provide an enhanced tactile impression from both sides. Such an execution is believed to be particularly desirable for such applications as leg cuffs, waistbands, side panels, and other aspects of absorbent articles such as diapers where a wearer may contact both opposing surfaces of the composite sheet material.

Embodiments of the present invention are also contemplated wherein the absorbent core is not joined to the backsheet 247, and/or the topsheet 249 in order to provide greater extensibility in the front waist region 246 and the rear waist region 245.

The absorbent core 275 may be any absorbent member which is generally compressible, conformable, non-irritating to the wearer's skin, and capable of absorbing and retaining fluids such as urine and other certain body exudates. As shown in FIG. 7, the absorbent core 275 has a garment-facing side, a body-facing side, a pair of side edges, and a pair of waist edges. The absorbent core 275 may be manufactured in a wide variety of sizes and shapes (e.g., rectangular, hourglass, "T"-shaped, asymmetric, etc.) and from a wide variety of fluid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 275 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 275 may also be varied to accommodate wearers ranging from infants through adults. However, the total absorbent capacity of the absorbent core 275 should be compatible with the design loading and the intended use of the diaper 250.

One embodiment of the diaper 250 has an asymmetric, modified T-shaped absorbent core 275 having ears in the front waist region but a generally rectangular shape in the rear waist region. Exemplary absorbent structures for use as the absorbent core 275 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The topsheet 249 is preferably positioned adjacent the inner surface of the absorbent core 275 and is preferably joined thereto and to the backsheet 247 by attachment means (not shown) such as those described above with respect to joining the backsheet 249 to the absorbent core 247. In a preferred embodiment of the present invention, the topsheet 249 and the backsheet 247 are joined directly to each other in the diaper periphery and are indirectly joined together by directly joining them to the absorbent core 275 by any suitable means.

The topsheet 249 is preferably compliant, soft feeling, and non-irritating to the wearer's skin. Further, the topsheet 249 is preferably fluid previous permitting fluids (e.g., urine) to readily penetrate through its thickness. A suitable topsheet 249 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 249 is preferably made of a hydrophobic material to isolate the wearer's skin from fluids which have passed through the topsheet 249 and are contained in the absorbent core 275 (i.e. to prevent rewet). If the topsheet 249 is made of a hydrophobic material, at least the upper surface of the topsheet 249 is treated to be hydrophilic so that fluids will transfer through the topsheet more rapidly. This diminishes the likelihood that body exudates will flow off the topsheet 249 rather than being drawn through the topsheet 249 and being absorbed by the absorbent core 275. The topsheet 249 can be rendered hydrophilic by treating it with a surfactant. Suitable methods for treating the topsheet 249 with a surfactant include spraying the topsheet 249 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein. As mentioned in the background discussion above, such hydrophilic materials tend to reduce the surface tension of bodily fluids discharged into an absorbent article, which increases the likelihood of liquid seepage if there are pores or pinholes in the backsheet of the article.

An alternative preferred topsheet comprises an apertured formed film. Apertured formed films are preferred for the topsheet because they are previous to body exudates and yet non-absorbent and have a reduced tendency to allow fluids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference.

It may also be desirable to provide the disposable absorbent article of the present invention with extensibility or elasticity in all or a portion of the side panels 290. (As used herein, the term "extensible" refers to materials that are capable of extending in at least one direction to a certain degree without undue rupture. The terms "elasticity" and "elastically extensible" refer to extensible materials that have the ability to return to approximately their original dimensions after the force that extended the material is removed. As used herein, any material or element described as "extensible" may also be elastically extensible unless otherwise provided.) Extensible side panels 290 provide a more comfortable and contouring fit by initially conformably fitting the diaper to the wearer and sustaining this fit throughout the time of wear well passed when the diaper has been loaded with exudates since the side panels allow the sides of the diaper to expand and contract. Extensible side panels 290 further provide more effective application of the diaper 250 since even if the diaperer pulls one side panel 290 farther than the other during the application (asymmetrically), the diaper 250 will "self-adjust" during wear. While the extensible side panels 290 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and in U.S. Pat. No. 5,151,092 issued to Buell et al. on Sep. 29, 1992; each of which are incorporated herein by reference.

The extensible side panels, or any other elements of the diaper 250 in which extensibility or elasticity is desirable such as the waistbands may comprise materials that have been "prestrained", or "mechanically prestrained" (i.e., subjected to some degree of localized pattern mechanical stretching to permanently elongate the material), or structural elastic-like webs, as described in U.S. Pat. No. 5,518,801 issued to Chappell et al. on May 21, 1996. The materials may be prestrained using deep embossing techniques as are known in the art. Alternatively, the materials may be prestrained by directing the material through an incremental mechanical stretching system as described in U.S. Pat. No. 5,330,458 issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

The diaper 250 preferably further comprises elastic leg features 272 for providing improved containment of fluids and other body exudates. Each elastic leg feature 272 may comprise several different embodiments for reducing the leakage of body exudates in the leg panels 282 (the elastic leg feature can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free fluids within the garment. Each of these patents are incorporated herein by reference.

While each elastic leg feature 272 may be configured so as to be similar to any of the leg bands, side flaps, barrier cuffs, or elastic cuffs described above, it is preferred that each elastic leg feature 272 comprise at least an inner barrier cuff comprising a barrier flap and a spacing element such as described in the above-referenced U.S. Pat. No. 4,909,803. In a preferred embodiment, the elastic leg feature 272 additionally comprises an elastic gasketing cuff 263 with one or more elastic strands 265, positioned outboard of the barrier cuff such as described in the above-referred U.S. Pat. No. 4,695,278.

The diaper 250 preferably further comprises an elastic waist feature 274 that provides improved fit and containment. The elastic waist feature 274 is that portion or zone of the diaper 250 which is intended to elastically expand and contract to dynamically fit the wearer's waist. The elastic waist feature 274 preferably extends longitudinally outwardly from at least one of the waist edges of the absorbent core 275 and generally forms at least a portion of the end edge of the diaper 250. Disposable diapers are generally constructed so as to have two elasticized waistbands, one positioned in the rear waist region and one positioned in the front waist region, although diapers can be constructed with a single elasticized waistband. Further, while the elastic waist feature 274 or any of its constituent elements can comprise a separate element affixed to the diaper 250, the elastic waist feature 274 may be constructed as an extension of other elements of the diaper such as the backsheet 247 or the topsheet 249, preferably both the backsheet 247 and the topsheet 249. Embodiments are also contemplated wherein the elastic waist feature 274 comprises apertures, as described above, to provide breathability in the waist regions. The elastic waist feature 274 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell; each of these references being incorporated herein by reference.

The diaper 250 also comprises a fastening system 276 which forms a side closure which maintains the rear waist region 245 and the front waist region 246 in an overlapping configuration such that lateral tensions are maintained around the circumference of the diaper to maintain the diaper on the wearer. Exemplary fastening systems are disclosed in U.S. Pat. No. 3,848,594 issued to Buell on Nov. 19, 1974; U.S. Pat. No. 4,662,875 issued to Hirotsu and Robertson on May 5, 1987; U.S. Pat. No. 4,869,724 issued to Scripps on Sep. 26, 1989; U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; and U.S. Pat. No. 5,326,612 entitled "Nonwoven Female Component For Refastenable Fastening Device And Method of Making the Same"issued to David J. K. Goulait on Jul. 5, 1994. Each of these patents are incorporated herein by reference.

Figure 9:
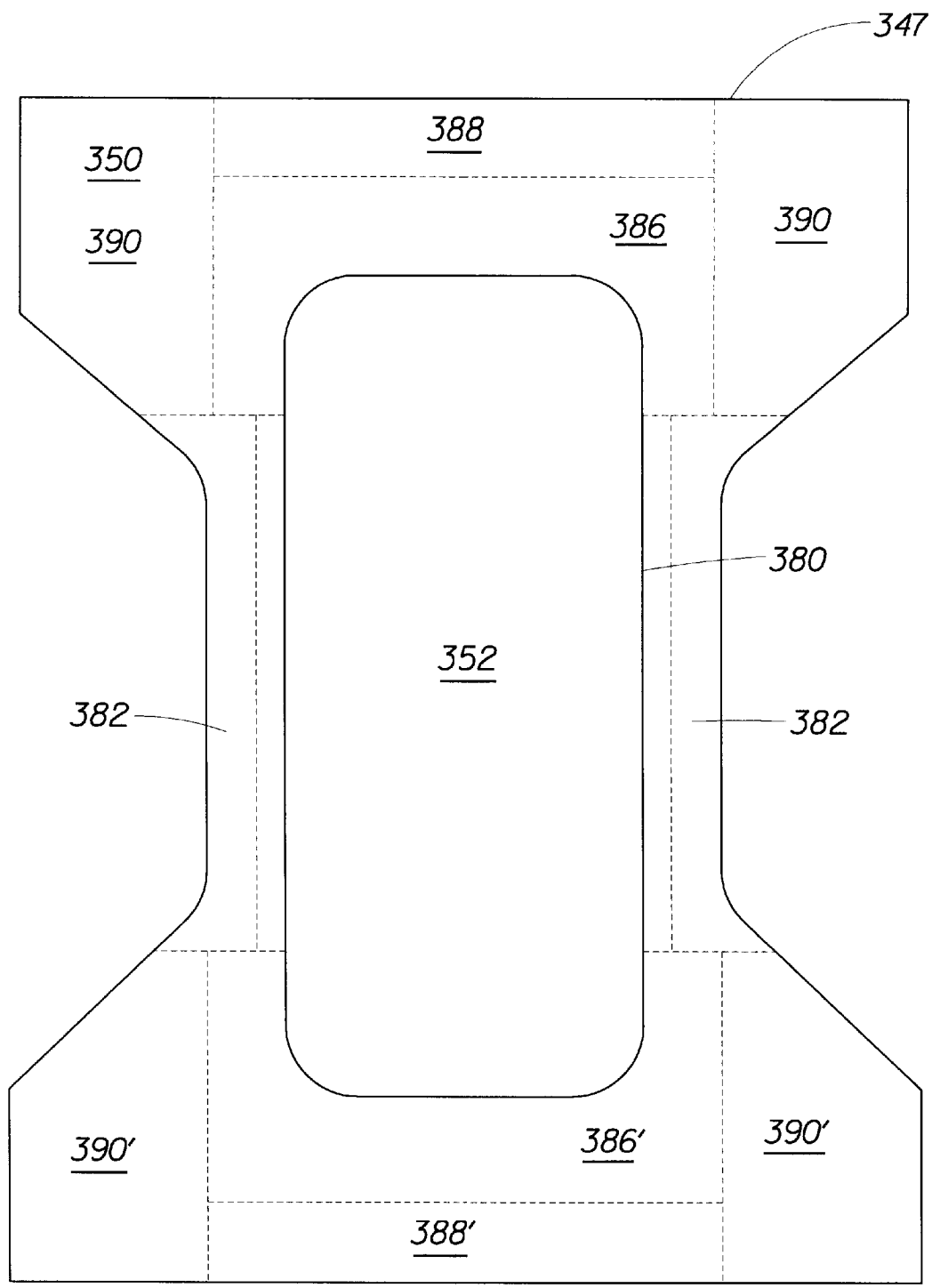
FIG. 9 is a plan view of another embodiment of a diaper backsheet of the present invention.

FIG. 9 shows a plan view of an alternative embodiment of the diaper backsheet of the present invention, with the portion of the backsheet positioned adjacent to the absorbent core facing the viewer. As shown in FIG. 9, the backsheet 347 comprises two layers 350 and 352. Layers 350 and 352 may be secured together by any suitable attachment means such as those described above. In this embodiment, layer 350 forms the outer surface of the diaper and layer 352 is positioned adjacent to the absorbent core. Since layer 350 is that portion of the backsheet 347 which will come into contact with the wearer's skin, layer 350 is preferably soft and comprises a nonwoven web. In addition to being soft, layer 350 is preferably moisture vapor permeable. Layer 352 preferably exhibits a moisture vapor transmission rate, of at least about 2000 $g/m^2/24$ hr., more preferably at least about 3000 $g/m^2/24$ hr., most preferably at least about 5000 $g/m^2/24$ hr. Since layer 350 does not need to prevent leakage of exudates absorbed and contained within the absorbent core, selection of materials that provide the desired softness and breathability is quite extensive. Suitable materials include, but are not limited to, nonwoven webs such as spunbond webs, meltblown webs, carded webs and the like. The nonwoven webs for layer 350 may comprise synthetic fibers, natural fibers, multi-component fibers such as bi-component fibers, or mixtures and blends thereof.

Layer 352 is the portion of the backsheet 347 which will prevent the exudates absorbed and contained in the absorbent core from wetting articles which contact the diaper. In order to protect the user against unwanted leakage of exudates absorbed and contained within the absorbent core, layer 352 should have width and length dimensions greater than those of the absorbent core. If layer 352 is not large enough exudates absorbed and contained in the absorbent core may find their way through the outer layer 350 during normal usage conditions. In the embodiment shown in FIG. 9, the absorbent core is preferably positioned in the main panel 380 and extends into the medial panels 386 and 386'. Accordingly, layer 352 is positioned within the main panel 380 and extends into the medial panels 386 and 386'. Layer 352 has length and width dimensions at least as large as those of the absorbent core and preferably greater than those of the absorbent core. If desired, layer 352 may extend beyond the main panel 380 and the medial panels 386 and 386' to into the leg panels 382, the waistband panels 388 and 388', and the side panels 390 and 390'. In addition, layer 352 may extend laterally and longitudinally outwardly from the main panel 380 to form portions of the periphery of the disposable diaper.

While layer 350 provides a substantial amount of moisture vapor permeability for the diaper, layer 352 should also be moisture vapor permeable in order to provide additional comfort for the wearer. In the embodiment of the invention shown in FIG. 9, layer 352 is comprised of the composite sheet 10 described above.

While a presently preferred embodiment of an absorbent article such as diaper 250 according to the present invention utilizes a composite sheet 10 according to the present invention for substantially the full extent of the backsheet 247, it is to be understood that the absorbent articles are in no way limited to such an embodiment. For example, a backsheet could be constructed from multiple backsheet elements having similar or diverse properties and constructions as described above with regard to FIG. 9. One such approach would be to form a backsheet with an external facing surface of a unitary or composite nonwoven layer as a substrate with the film layer comprising only the region of the backsheet where fluid imperviousness is desired, such as, for example, the region corresponding to the region 352 depicted in FIG. 9.

Moreover, it may also be desirable for certain applications to reverse the orientation of the layers 350 and 352 of FIG. 9 so as to place the film layer on the external or garment-facing side of the backsheet and the fibrous substrate layer on the internal or absorbent-core-facing side of the backsheet. It may also likewise be desirable to utilize the composite sheet 10 in the dual-sided embodiment of FIG. 2 wherein both sides of the backsheet would be faced with a fibrous layer. All such variations are contemplated as being within the scope of the present invention. Moreover, depending upon the specific application, the properties provided by the composite sheets of the present invention may also be employed to great advantage in other regions of the absorbent article besides the central portion of the backsheet which overlies the absorbent core structure. For example, the desirable fluid impervious, moisture-vapor-pervious properties of the composite sheet also provide desirable attributes for peripheral portions of the absorbent article which extend laterally outwardly from the marginal edges of the absorbent core such as the side panels 290, 290' depicted in FIG. 8. Other such "peripheral portions" of the absorbent article for which such attributes may be desirable are in the vicinity of the leg panels 282 including but not limited to various bands, cuffs, and flaps.

Likewise, while much of the foregoing discussion has focused upon the representative absorbent article in the form of diaper 250, it is to be understood that the materials and principles of the present invention are equally applicable to other absorbent articles such as incontinence briefs, incontinence undergarments, diaper holders and liners, feminine hygiene products (sanitary napkins, pantiliners, etc.), training pants, pull-on garments, and the like wherein the materials of the present invention may be employed advantageously. By way of illustration, a backsheet of a sanitary napkin according the present invention could be formed from a composite sheet of the present invention, as could peripheral portions of a sanitary napkin such as wings or side flaps.

After manufacture of the composite sheet 10, and either before or after the sheet's incorporation into an absorbent article, it may be desirable to subject the sheet to a post-formation mechanical process such as creping, straining/activation by rolling with corrugated rolls, or otherwise. One such representative process is described in detail in U.S. Pat. No, 5,518,801 to Chappell et al., the disclosure of which is hereby incorporated herein by reference.

INTERNAL ENVIRONMENTAL CONDITIONS

As discussed above, an important characteristic which is indicative of the improved performance of the sheet materials of the present invention is the environmental humidity within the interior of the absorbent article under in-use conditions. In order to accurately and consistently characterize the humidity within the absorbent article, it is necessary to describe the locations of measurement and the procedure for measurement of the humidity. These measurements are made relative to the crotch point.

The "crotch point" of an article and the article's absorbent core is determined (See FIG. 12) by placing the article on a wearer and positioning the wearer in a fully-erect standing position and then placing a highly extensible filament 603 around the legs 601 and 602 in a figure eight configuration. The point in the article and the absorbent core corresponding to the point of intersection 604 of the filament is deemed to be the crotch point of the article and the absorbent core. It is understood that the crotch point is determined by placing the absorbent article on a wearer in the intended manner and determining where the crossed filament would contact the article/core.

As referred to herein, the "crotch region" of an absorbent core corresponds to 50% of the absorbent core's total length (i.e., in the y-dimension), where the crotch point is located in the longitudinal center of the crotch region. That is, the crotch region is determined by first locating the crotch point of the absorbent core, and then measuring forward and backward a distance of 25% of the core's total length. The temperature and humidity measurement points correspond to the intersection of the transverse lines defining the crotch region and the longitudinal centerline. The evaporimeter point corresponds to the intersection of the transverse line at the rear of the crotch region and the longitudinal centerline.

Figure 10:
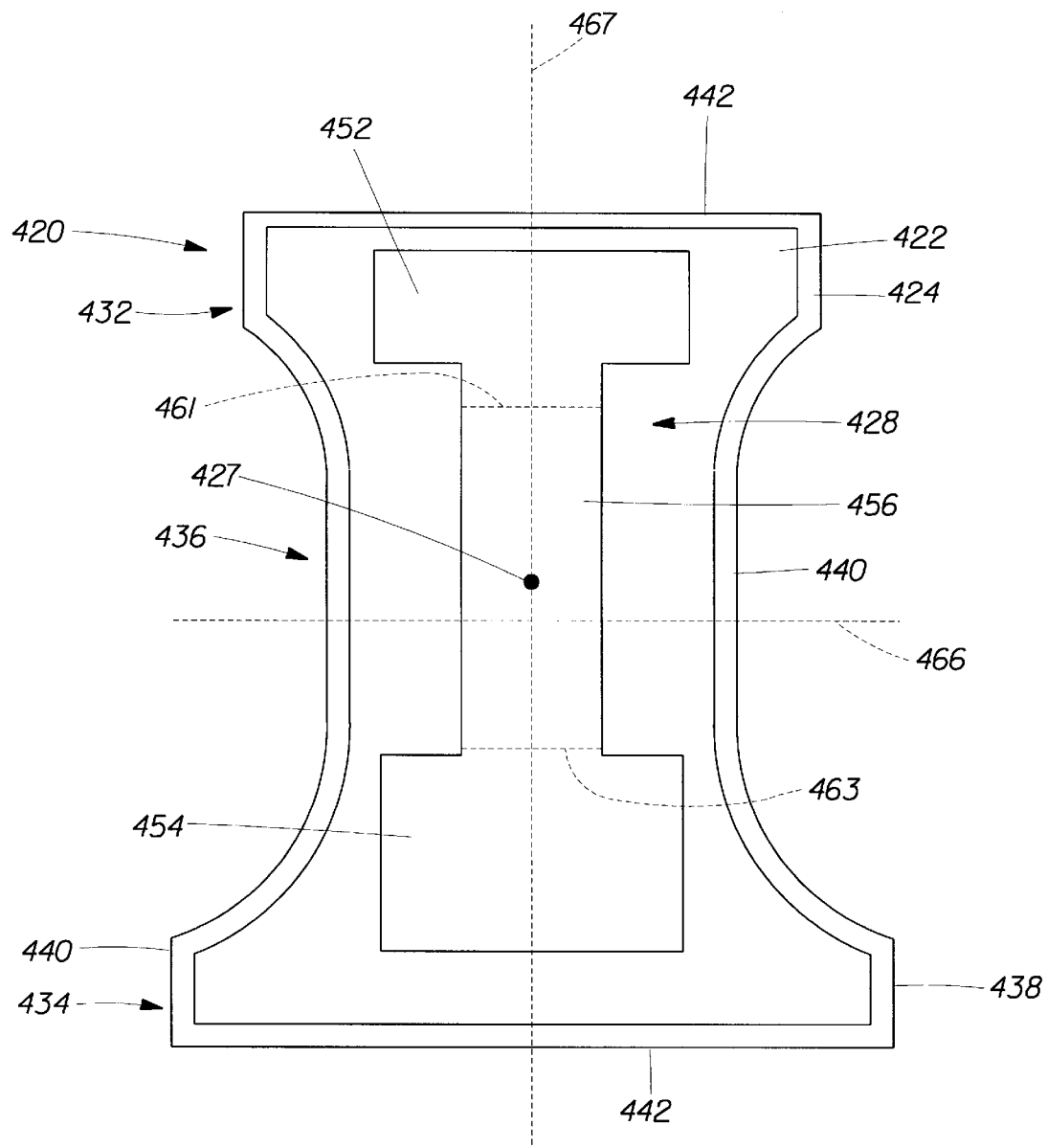
FIG. 10 is a plan view of a disposable diaper of the present invention in its flat uncontracted condition illustrating various zones and defined positions of the diaper.

Referring now to FIG. 10, the crotch region is defined by determining the crotch point of core 428 in accordance with the description herein. As discussed above, the crotch point is determined by reference to the wearer's anatomy. For purposes of illustration only, the crotch point of core 428 is depicted as item 427 in FIG. 10. Crotch point 427 is depicted as being located on the longitudinal centerline 467 of diaper 420 and absorbent core 428. This will generally be the case, regardless of the configuration of the diaper and absorbent core. However, as indicated, crotch point 427 is not located on transverse centerline 466 in this particular embodiment, though it may be in other diaper/core designs. As is discussed above, once the crotch point of absorbent core 428 is determined, the crotch region is determined by measuring forward from the crotch point a distance of 25% of the core's total length (depicted as transverse line 461) and backward from the crotch point a distance of 25% of the core's total length (depicted as transverse line 463). In this illustration, the crotch region is the region of the core located between transverse lines 461 and 463. The temperature and humidity measurement points correspond to the intersection of the transverse lines, 461 and 463, which define the crotch region and the longitudinal centerline, 467. The evaporimeter point is the point at which the transverse line 463 intersects the longitudinal centerline 467. This point is the point at which the evaporimeter measure of vapor transmission through the outer cover is determined. As depicted in FIG. 10, absorbent core 428 is shown to have a front region 452, a back region 454, and a crotch region 456. Again, the crotch region 456 of core 428 is dictated by the location of the crotch point in the core.

Figure 11:
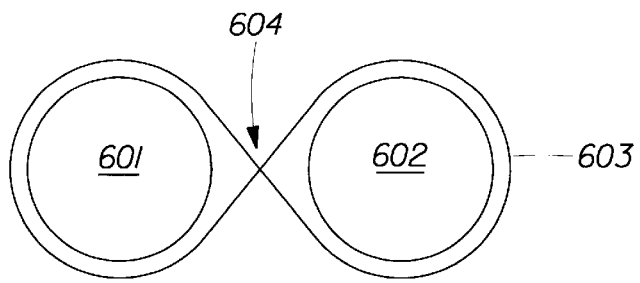
FIG. 11 is a plan view of an absorbent core suitable for use in absorbent articles in accordance with the present invention.

The absorbent core 428 will comprise any absorbent means which is capable of absorbing and retaining liquids such as urine and other certain body exudates, and which is capable of providing the fluid distribution/storage properties which define the present invention. While absorbent core 428 is depicted in FIG. 10 in an "I" configuration, any shape may be utilized. For example, an absorbent core 528 is shown in FIG. 11 in an "hour glass" configuration, wherein the core has arcuate cutouts in its longitudinal edges, indicated generally as 542. For illustration purposes, the crotch point is identified by item 527. (As discussed above, the crotch point of the absorbent core is extrapolated from the wearer.) As shown, the crotch point 527 generally lies on longitudinal center line 567 and on transverse line (though not the center transverse line in this embodiment) 568. The crotch region is determined by measuring forward from the crotch point a distance of 25% of the core's total length (depicted as transverse line 561) and backward from the crotch point a distance of 25% of the core's total length (depicted as transverse line 563). The temperature and humidity measurement points correspond to the intersection of the transverse lines, 561 and 563, which define the crotch region and the longitudinal centerline, 567. The evaporimeter point is the point at which the transverse line 563 intersects the longitudinal centerline 567. This point is the point at which the evaporimeter measure of vapor transmission through the outer cover is determined. The crotch region 556, is the region of the core between transverse lines 561 and 563. In addition to crotch region 556, core 528 has a front region 552 and a rear region 554.

Figure 12:
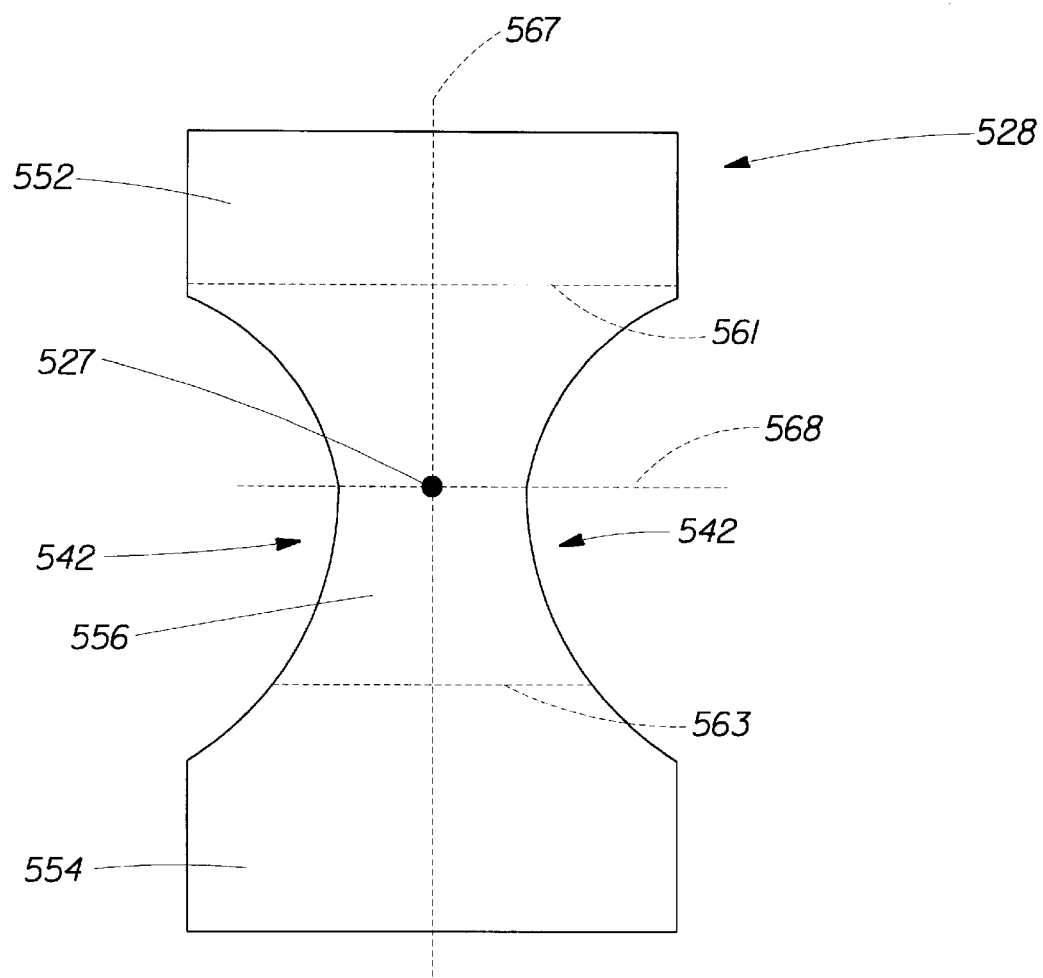
FIG. 12 is an illustration depicting the approach to determining the crotch point of an absorbent article with reference to the wearer.

FIG. 12 illustrates the means for determining the crotch point of an article and its absorbent core. Referring to FIG. 12, the legs of a standing wearer are depicted in cross-section as 601 and 602. A continuous material 603 (e.g., an elastomeric string or rubberband) is twisted once and is placed around the wearer's legs at a point sufficiently close to the wearer's torso such that the intersection 604 of material 603 can be extrapolated onto the article being worn. The crotch point of the core of the article is thereby determined, and the crotch region of the core is determined per the above description.

In accordance with the present invention, absorbent articles utilizing the composite sheet materials described herein will preferably exhibit an MVTR of at least about 3000 $g/m^2/24$ hrs, more preferably at least about 4000 $g/m^2/24$ hrs, and most preferably at least about 5000 $g/m^2/24$ hrs. Such absorbent articles preferably also exhibit a moisture impact value of less than about 1 $g/m^2$ @ 2400 joules/$m^2$, and more preferably less than about 0.75 $g/m^2$ @ 2400 joules/m2. Regarding internal environmental conditions, such absorbent articles preferably exhibit a dry back humidity of less than about 75%, more preferably less than about 70%, still more preferably less than about 60%, and most preferably less than about 50%, and a wet back humidity of less than about 85%, more preferably less than about 75%. In terms of moisture vapor transmission, such articles preferably exhibit an evaporimeter reading of greater than about 10 $g/m^2/hr$, more preferably greater than about 15 $g/m^2/hr$, and most preferably greater than about 25 $g/m^2/hr$.

ABSORBENT ARTICLE TEST METHODS

A. Article Testing to Determine Vapor Transmission Through the Outer Cover and Environmental Relative Humidity and Temperature The following protocol is intended to provide the evaporimeter measure of vapor transmission through the outer cover, as well as, the relative humidity and temperature inside the article in both the front and the rear. The protocol uses data determined from in-use testing of test articles by panelists.

Panelist and Wearer Selection

1. Article wearers should be recruited by weight, within the intended size range of the articles being tested. Currently, the article sizes and baby weights for marketed Pampers, Luvs and Huggies are as follows (as of Mar. 25, 1997):

| Diaper Size | Newborn | Small | Small/Medium | Medium | Large | X-Large |
|---|---|---|---|---|---|---|
| Pampers | up to 10 lbs | 8–14 lbs | 12–18 lbs | 16–28 lbs | over 22 lbs | over 27 lbs |
| Luvs | na | 8–15 lbs | 12–18 lbs | 16–28 lbs | 21–37 lbs | over 30 lbs |
| Huggies | up to 10 lbs | 8–14 lbs | 12–18 lbs | 16–28 lbs | 22–37 lbs | over 30 lbs |

2. A group of 100 wearers should be recruited uniformly across the appropriate weight range relative to the size of articles being tested and the intended user group. The group should be comprised of 50% male and 50% female wearers. Note: the above sizes are for currently marketed articles and may change as article designs and or sizes are modified.

3. Following the recruiting step, 30 wearers, 15 male and 15 female, are to be selected from their respective gender group, at random.

Article Setup

1. The test articles are weighed to provide a dry article weight.

2. The longitudinal centerline is marked on the outer cover in a permanent fashion.

3. The total core length is determined by measuring the length of the core while the article is held in the flat uncontracted state.

4. The panelist, parent or guardian in the instance of diaper articles, removes the article the child is wearing when the test begins, i.e. the panelist's own article, and the panelist applies the test article to the wearer in the panelist's normal fashion.

5. Once the test article is applied, the panelist places the wearer in the standing position with the wearers feet shoulder width apart and the crotch point is determined as previously described in this application.

6. The crotch point is then marked on the outside of the test article in a permanent fashion.

7. In addition, the temperature and humidity points, as well as, the evaporimeter point are then marked on the outside of the test article in a permanent fashion. These points are determined by measuring forward and backward from the crotch point a distance equal to 25% of the total core length.

8. The distance from the temperature and humidity points to the end of the article in both the front and rear is measured. This distance corresponds to the length of the temperature and humidity probe and/or wiring to be inserted into the article when the measurement is taken.

9. The loading zone is then determined by measuring from the crotch point forward to the appropriate genital point relative to the sex and size of the wearer. The distance forward from the crotch point for females in the large size is 1.25 inches. The distance forward from the crotch point for males in the large size range is 2.5 inches.

10. It is apparent to one skilled in the art that these distances may increase or decrease with the size of the wearer. Therefor, for the other sizes, the distance can be determined by placing the wearer in a standing position and determining the crotch point as specified previously, and then measuring from the crotch point to the urethra or base of the penis.

11. Once the loading zone is determined, the distance from the front waist to the loading zone is measured; this distance is used to establish the length of the loading tube to be inserted into the article during the synthetic urine loading.

Synthetic urine

1. The test fluid to be used for the test is synthetic urine (syn-urine). This aqueous composition comprises the following components dissolved in distilled water:

| Component | Percentage |
|---|---|
| KCl | 2.0 g/L |
| Na2SO4 | 2.0 g/L |
| (NH4)H2PO4 | .85 g/L |
| (NH4)2HPO4 | .15 g/L |
| CaCl2 | .19 g/L |
| MgCl2 | .23 g/L |

2. The temperature of the syn-urine in the syn-urine bath is to be held at 37° C. A suitable heated bath is Lauda M20-B available from VWR Scientific Products.

3. Delivery pumps are to be used to pump the syn-urine from the heated bath to the article. The volume and rate of delivery is to be 75 ml at 15 mls/sec. Suitable pumps include Masterflex Models 7550-60 or 7524-00 available from Cole Parmer Instrument Company. The inner diameter of the loading tube is to be 0.125 inch.

Temperature and Humidity Probes

The temperature Humidity Probes are model # 880F available from General Eastern Instruments, 20 Commerce Way, Woburn Mass. 01801.

Evaporimeter Equipment

A suitable evaporimeter can be purchased from Cyberderm, 275 New Darlington Road, Media, Pa. 19063-5607. Model 2155 Evaporimeter Ep-2 is suitable for this purpose.

Test Protocol

1. The following protocol is to be conducted in an environmentally control room with the temperature controlled at 70° F. +/−3° F. and the Humidity controlled at 40% +/−3%.

2. Once the articles are applied and marked as described above, the wearers are allowed to wear the articles for 15 minutes. Following the 15 minute wear time, the temperature and humidity both in the front and rear of the articles is determined by inserting the probes to the predetermined distance as measured from the waist edges of the article.

3. No outer garments are to be worn over the diapers.

4. All temperature and humidity measurements are taken 2 minutes after the probes are inserted into the article.

5. Following the "Dry" product temperature and humidity measurements, the test articles are then loaded by inserting the loading tube to the predetermined distance, as measured from the front waist edge of the article, and applying the specified loading at the specified rate.

6. Between loads, the wearers are allowed to return to normal activity.

7. The articles are loaded with the specified load and rate every 15 minutes, i.e. 15 minute intervals between loads.

8. Four loads as described above are applied to the articles.

9. Following the last loading, the wearers are allowed to return to normal activity for an additional 15 minutes. Following the 15 minutes, the temperature and humidity are determined by inserting the probes into the article at the predetermined depth. The probes are to be placed along the longitudinal centerline of the product.

10. After the loaded diaper temperature and humidity are determined the probes are removed and the wearer is placed on their belly for the evaporimeter measurement. The evaporimeter is placed on the outer cover at the transverse line at the rear of the crotch region, in the center of the product. The probe is left in place for 1 minute. At 1 minute the measurement is recorded. The probe must be kept in contact with the outer cover and as vertical an orientation as possible.

PREPARATION OF EXAMPLE ABSORBENT ARTICLES

Figure 13:
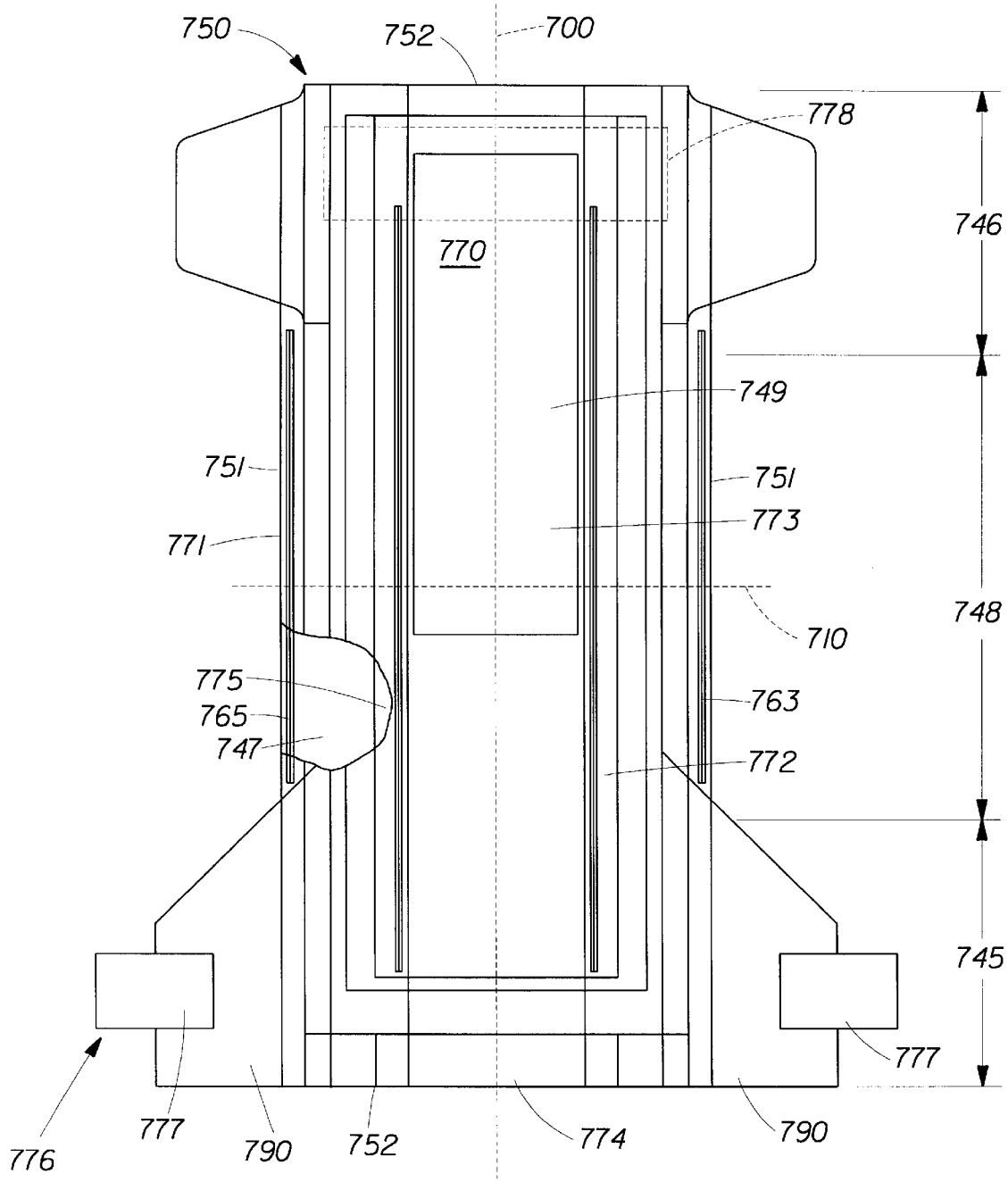
FIG. 13 is a plan view of an absorbent article in accordance with the product test protocol described herein.

The basic diaper design used to construct the products used in the environmental conditions test is based in part on diaper 750, shown in FIG. 13. FIG. 13 is a plan view of the diaper 750 of the present invention in its flat-out, uncontracted state (i.e., with elastic induced contraction pulled out) with portions of the structure being cut-away to more clearly show the construction of the diaper 750. As shown in FIG. 13, the diaper 750 comprises a containment assembly 770 comprising a topsheet 749; a backsheet 747 joined to the topsheet; and an absorbent core 775 positioned between the topsheet 749 and the backsheet 747. The absorbent core 775 has a pair of opposing longitudinal edges, an inner surface and an outer surface. The diaper further comprises elastic leg features 772; elastic waist features 774; and a fastening system 776 comprising a pair of securement members 777 and a landing member 778. The topsheet material used for Codes A and C were the same. The topsheet was a polypropylene nonwoven available from Fibertech, Landisville N.J., under the trade designation of P-8.

The diaper 750 is shown in FIG. 13 with the portion of the diaper 750 which faces the wearer, the inner surface 773, facing the viewer. The diaper 750 is shown in FIG. 13 to have an inner surface 773 (facing the viewer in FIG. 13), an outer surface 771 opposed to the inner surface 773, a rear or back waist region 745, a front waist region 746 opposed to the rear waist region 745, a crotch region 748 positioned between the rear waist region 745 and the front waist region 746, and a periphery which is defined by the outer perimeter or edges of the diaper 746 in which the longitudinal or side edges are designated 751 and the end edges are designated 752. The inner surface 773 of the diaper 750 comprises that portion of the diaper 750 which is positioned adjacent to the wearer's body during use (i.e., the inner surface 773 generally is formed by at least a portion of the topsheet 749 and other components joined to the topsheet 749). The outer surface 771 comprises that portion of the diaper 750 which is positioned away from the wearer's body (i.e., the outer surface 771 is generally formed by at least a portion of the backsheet 747 and other components joined to the backsheet 747). The rear waist region 745 and the front waist region 746 extend from the end edges 752 of the periphery to the crotch region 748.

The diaper 750 also has two centerlines, a longitudinal centerline 700 and a transverse centerline 710. The term "longitudinal", as used herein, refers to a line, axis, or direction in the plane of the diaper 750 that is generally aligned with (e.g. approximately parallel with) a vertical plane which bisects a standing wearer into left and right halves when the diaper 750 is worn. The terms "transverse" and "lateral", as used herein, are interchangeable and refer to a line, axis or direction which lies within the plane of the diaper that is generally perpendicular to the longitudinal direction.

FIG. 13 shows the containment assembly 770 in which the topsheet 749 and the backsheet 747 have length and width dimensions generally larger than those of the absorbent core 775. The topsheet 749 and the backsheet 747 extend beyond the edges of the absorbent core 775 to thereby form the periphery of the diaper 750.

In all of the products tested, the backsheet 747 comprised a continuous sheet or layer which defined the front waist region 746, the rear waist region 745, and the crotch region 748. As used herein, the term "layer" does not necessarily limit the element to a single strata of material in that a layer may actually comprise laminates or combinations of sheets or webs of the requisite types of materials. In fact, Products A and B were laminate structures comprised of film layers and fibrous substrates. The backsheet 747 has an inner surface and an opposed outer surface. The inner surface is that portion of the backsheet 747 which is positioned adjacent the absorbent core. The outer surface of the backsheet 747 corresponds to the outer surface 771 of the diaper 750. The composite structure utilized as the backsheet material for Code A is the same as the composite structure disclosed as example 24. The material used as the backsheet for Code C is XBF-100W available from the Exxon Corporation.

The absorbent core 775 may be any absorbent member which is generally compressible, conformable, non-irritating to the wearer's skin, and capable of absorbing and retaining fluids such as urine and other certain body exudates. The absorbent core of Code B was the same as Huggies Supreme Breathable products absorbent core as these products were purchased co mmercially. The absorbent core of both Codes A and C were the same and were shaped as shown by absorbent core 775, rectangular. The composition of Code B is not completely known, however, it is believed that the composition of all three products tests, Codes A, B and C do contain comminuted wood pulp, meltblown or carded polymers, tissue and superabsorbent polymers. Codes A and C also contain chemically stiffened, modified or cross-linked cellulosic fibers.

All three products had some degree of extensibility or elasticity in all or a portion of the side panels 790. (As used herein, the term "extensible" refers to materials that are capable of extending in at least one direction to a certain degree without undue rupture. The terms "elasticity" and "elastically extensible" refer to extensible materials that have the ability to return to approximately their original dimensions after the force that extended the material is removed. As used herein, any material or element described as "extensible" may also be elastically extensible unless otherwise provided.) Extensible side panels 790 provide a more comfortable and contouring fit by initially conformably fitting the diaper to the wearer and sustaining this fit throughout the time of wear well passed when the diaper has been loaded with exudates since the side panels allow the sides of the diaper to expand and contract. Extensible side panels 790 further provide more effective application of the diaper 750 since even if the diaperer pulls one side panel 790 farther than the other during the application (asymmetrically), the diaper 750 will "self-adjust" during wear.

The extensible side panels of Codes A and C were comprised of materials that have been "prestrained", or "mechanically prestrained" (i.e., subjected to some degree of localized pattern mechanical stretching to permanently elongate the material), or structural elastic-like webs, as described in U.S. Pat. No. 5,518,801 issued to Chappell et al. on May 21, 1996.

The diaper 750 further comprises elastic leg features 772 for providing improved containment of fluids and other body exudates. Each elastic leg feature 772 may comprise several different embodiments for reducing the leakage of body exudates in the leg panels (the elastic leg feature can be and is sometimes also referred to as leg bands, side flaps, barrier cuffs, or elastic cuffs.)

All diapers had features similar to elastic leg feature 772. Codes A and C were exactly like elastic leg feature 772. Products Codea A and C had both an inner barrier cuff comprising a barrier flap and a spacing element and an additional elastic gasketing cuff 763 with one or more elastic strands 765, positioned outboard of the barrier cuff.

The diaper 750 further comprised an elastic waist feature 774 that provides improved fit and containment. The elastic waist feature 774 is that portion or zone of the diaper 750 which is intended to elastically expand and contract to dynamically fit the wearer's waist. The elastic waist feature 774 extends longitudinally outwardly from at least one of the waist edges of the absorbent core 775 and generally forms at least a portion of the end edge of the diaper 750. Codes A and C had a single elasticized waistband positioned in the rear waist region. Code B had waistbands in both the front and rear waist regions.

The diaper 750 also comprises a fastening system 776 which forms a side closure which maintains the rear waist region 745 and the front waist region 746 in an overlapping configuration such that lateral tensions are maintained around the circumference of the diaper to maintain the diaper on the wearer.

The absorbent articles according to Product Codes A, B, and C were evaluated according to the protocol of the foregoing Test Method and the results are presented in Table A1:

TABLE A1

|  | Code A | Code B | Code C |
| --- | --- | --- | --- |
| Backsheet MVTR | 3,400 | 1,300 | 4,500 |
| Dry Diaper |  |  |  |
| Back Humidity | 49 | 50 | 42 |
| Loaded Diaper |  |  |  |
| Back Humidity | 80 | 89 | 72 |
| TEWL (g/m2/hr) | 22 | 16 | 24 |
| Diaper Loading | 317 | 312 | 327 |

Moisture impact data for the backsheet material utilized in these three products is presented in Table A2:

TABLE A2

| Material | No Hold Moisture Impact (g/m2 @ 2,400 joules) | 10 Second Hold Moisture Impact (g/m2 @ 2,400 joules) |
| --- | --- | --- |
| Code C | 1.31 | 2.30 |
| Code B | 0.84 | 1.20 |
| Code A | 0.00 | 2.96 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

(a) a topsheet;

(b) a backsheet formed from a moisture vapor permeable, substantially liquid impermeable composite sheet material including a fibrous nonwoven substrate, said fibrous nonwoven substrate having opposite first and second planar sides and a moisture vapor permeable thermoplastic film bonded to the first side of said fibrous nonwoven substrate, said moisture vapor permeable film having an average thickness of less than 25 microns, said composite sheet exhibiting a peel strength of at least 0.1 N/cm, a dynamic fluid transmission of less than about 0.75 g/m$^2$ when subjected to an impact energy of about 2400 joules/m$^2$, a hydrostatic head of at least 60 cm, and having a moisture vapor transmission rate, according to the desiccant method, of at least 2800 g/m$^2$/24 hr.; and (c) an absorbent core located between said topsheet and said backsheet; wherein said absorbent article exhibits an evaporimeter measure through said backsheet of at least 10 g/m2/hr.

2. An absorbent article comprising:

(a) a topsheet;

(b) a backsheet formed from a moisture vapor permeable, substantially liquid impermeable composite sheet material including a fibrous nonwoven substrate, said fibrous nonwoven substrate having opposite first and second planar sides, and a moisture vapor permeable thermoplastic film bonded to the first side of said fibrous nonwoven substrate, said moisture vapor permeable film having an average thickness of less than 25 microns, said composite sheet exhibiting a peel strength of at least 0.1 N/cm, a dynamic fluid transmission of less than about 0.75 g/m$^2$ when subjected to an impact energy of about 2400 joules/m$^2$, a hydrostatic head of at least 60 cm, and having a moisture vapor transmission rate, according to the desiccant method, of at least 2800 g/m$^2$/24 hr.; and (c) an absorbent core located between said topsheet and said backsheet; wherein said absorbent article exhibits a dry back humidity of less than about 75%.

3. An absorbent article comprising:

(a) a topsheet;

(b) a backsheet formed from a moisture vapor permeable, substantially liquid impermeable composite sheet material including a fibrous nonwoven substrate, said fibrous nonwoven substrate having opposite first and second planar sides, and a moisture vapor permeable thermoplastic film bonded to the first side of said fibrous nonwoven substrate, said moisture vapor permeable film having an average thickness of less than 25 microns, said composite sheet exhibiting a peel strength of at least 0.1 N/cm, a dynamic fluid transmission of less than about 0.75 g/m$^2$ when subjected to an impact energy of about 2400 joules/m$^2$, a hydrostatic head of at least 60 cm, and having a moisture vapor transmission rate, according to the desiccant method, of at least 2800 g/m$^2$/24 hr.; and (c) an absorbent core located between said topsheet and said backsheet; wherein said absorbent article exhibits a wet back humidity of less than about 85%.

4. An absorbent article comprising:

(a) a topsheet;

(b) a backsheet formed from a moisture vapor permeable, substantially liquid impermeable composite sheet material including a fibrous nonwoven substrate, said fibrous nonwoven substrate having opposite first and second planar sides, and a moisture vapor permeable thermoplastic film bonded to the first side of said fibrous nonwoven substrate, said moisture vapor permeable film having an average thickness of less than 25 microns, said composite sheet exhibiting a peel strength of at least 0.1 N/cm, a dynamic fluid transmission of less than about 0.75 g/m² when subjected to an impact energy of about 2400 joules/m², a hydrostatic head of at least 60 cm, and having a moisture vapor transmission rate, according to the desiccant method, of at least 5000 g/m²/24 hr.; and (c) an absorbent core located between said topsheet and said backsheet.

5. The absorbent article of any one of claims 1 to 4, wherein said moisture vapor permeable film is comprised of at least about 50% by weight of polymer selected from the group of block copolyether esters, block copolyether amides, polyurethanes, polyvinyl alcohol, and combinations thereof.

6. The absorbent article of claim 5, wherein said moisture vapor permeable film has an average thickness of less than 20 microns.

7. The absorbent article of claim 6, wherein said composite sheet exhibits a hydrostatic head of at least 120 cm and a dynamic fluid transmission of less than about 0.5 g/m² when subjected to an impact energy of about 2400 joules/m².

8. The absorbent article of claim 6, wherein the composite sheet is substantially free of micoropores, and substantially no liquid moisture passes through the sheet when tested according to the liquid moisture seepage test.

9. The absorbent article of claim 8, wherein said composite sheet prevents passage of microbes when tested according to the ISO 11607 standard for sterile packaging materials.

10. The absorbent article of claim 9, wherein said composite sheet, when tested according to ASTM F1671, prevents the passage of microbe with a diameter greater than 0.025 microns.

11. The absorbent article of claim 6, wherein said moisture vapor permeable film consists essentially of a copolyether ester elastomer, and wherein said fibrous nonwoven substrate consists essentially of a blend of between 20% and 80% by weight polyolefin polymer fibers and between 20% and 80% by weight polyester polymer fibers.

12. The absorbent article of claim 11, wherein said polyester fibers are shaped fibers with a scalloped-oval cross-section and wherein the composite sheet has and a moisture vapor transmission rate, according to the dessicant method, of at least 3000 g/m²/24 hr.

13. The absorbent article of claim 6, wherein said moisture vapor permeable film is bonded to the fibrous substrate with a hotmelt adhesive applied between the fibrous nonwoven substrate and the moisture vapor permeable film at an adhesive basis weight between 0.5 and 5 mg/in², said adhesive contacting less than 75% of the surface of the first side of the fibrous nonwoven substrate.

14. The absorbent article of claim 13, wherein said fibrous nonwoven substrate consists essentially of polyolefin polymer fibers, and wherein said adhesive is applied between said fibrous nonwoven substrate and said moisture vapor permeable film at a weight of between 1 and 3 mg per 6.45 cm² of the first surface of the fibrous nonwoven substrate.

15. The absorbent article of claim 6, wherein said moisture vapor permeable film has first and second layers, each of said layers being comprised of a different moisture vapor permeable thermoplastic polymer composition.

16. The absorbent article of claim 15, wherein
said first layer of said moisture vapor permeable film comprises at least 60% of the total weight of the film and is comprises of a substantially hydrophilic layer,
said second layer of said moisture vapor permeable film comprises a substantially hydrophobic layer, and
said first layer of said moisture vapor permeable film abuts said fibrous substrate.

17. The absorbent article of claim 16, wherein said composite sheet further includes an additional layer of diverse construction is adhesively bonded to the second layer of said moisture vapor permeable film.

18. The absorbent article of claim 17, wherein said composite sheet had a wet bond strength of at least 80 g/cm.

19. The absorbent article of claim 17, wherein said additional layer comprises a microporous film.

20. The absorbent article of claim 6, wherein said composite sheet exhibits a hydrohead of at least 120 cm, a dynamic fluid transmission of less than about 0.65 g/m² when subjected to an impact energy of about 2400 joules/m², and a moisture vapor transmission rate, according to the dessicant method, of at least 3200 g/m²/24 hr.

21. The absorbent article of claim 20, wherein said moisture vapor permeable film of said composite sheet has an average thickness of less than 15 microns, and the basis weight of said fibrous substrate is between about of 13.5 and about 40 g/m².

22. The absorbent article of claim 21, wherein said moisture vapor permeable film of said composite sheet has an average thickness of less than 10 microns and a dynamic fluid transmission of less than about 0.5 g/m² when subjected to an impact energy of about 2400 joules/m², and a moisture vapor transmission rate, according to the dessicant method, of at least 3800 g/m²/24 hr.

* * * * *